United States Patent [19]

Toner et al.

[11] Patent Number: 5,523,402
[45] Date of Patent: Jun. 4, 1996

[54] TRIPYRIDYL MACROCYCLIC COMPOUNDS

[75] Inventors: John L. Toner, Downingtown, Pa.; David A. Hilborn, Henrietta; Bruce J. Murray, Walworth, both of N.Y.; Timothy Z. Hossain, Dallas, Tex.

[73] Assignee: Sterling Winthrop Inc., New York, N.Y.

[21] Appl. No.: 287,381

[22] Filed: Aug. 8, 1994

Related U.S. Application Data

[63] Continuation of Ser. No. 784,333, Oct. 29, 1991, Pat. No. 5,367,080, which is a continuation-in-part of Ser. No. 610,861, Nov. 8, 1990, abandoned.

[51] Int. Cl.⁶ .................................................. C07D 259/00
[52] U.S. Cl. ............................................. 540/474; 540/467
[58] Field of Search ...................................... 540/474, 467

[56] References Cited

U.S. PATENT DOCUMENTS

| | | | |
|---|---|---|---|
| 4,637,988 | 1/1987 | Hinshaw et al. | 436/546 |
| 4,670,572 | 6/1987 | Hinshaw et al. | 556/1 |
| 4,745,076 | 5/1988 | Muller et al. | 436/537 |
| 4,761,481 | 8/1988 | Hale et al. | 546/296 |
| 4,794,191 | 12/1988 | Hinshaw et al. | 549/211 |
| 4,801,722 | 1/1989 | Hinshaw et al. | 549/211 |
| 4,837,169 | 6/1989 | Toner et al. | 436/546 |
| 4,859,777 | 8/1989 | Toner et al. | 546/256 |
| 5,075,447 | 12/1991 | Muller et al. | 546/10 |
| 5,202,423 | 4/1993 | Kankare et al. | 530/391.5 |

*Primary Examiner*—Raymond Henley, III
*Assistant Examiner*—Phyllis G. Spivack
*Attorney, Agent, or Firm*—Fish & Richardson

[57] ABSTRACT

Tripyridyl macrocyclic compounds that are employed in the production of a complexing agent for use in targeting radioactive immunoreagents with the following formula are disclosed:

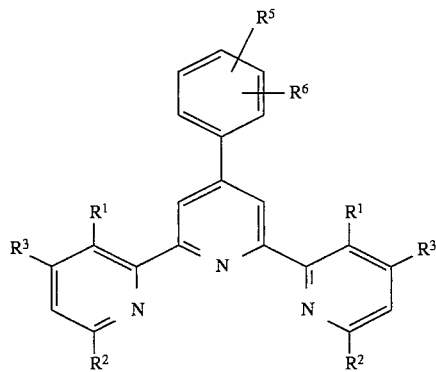

wherein $R^1$ represents hydrogen, alkyl, alkoxy, alkylthio, alkylamino, alkylformamido, aryl, aryloxy, heterocyclyl or a protein reactive group;

the two $R^2$ groups, taken together, represent a bridging group serving to complete a macrocyclic ring, the bridging group containing at least one heteroatom and at least one alkylene group which form part of the resulting macrocyclic ring;

$R^3$ represents hydrogen, alkyl, alkoxy, alkylthio, alkylamino, alkylformamido, aryl, aryloxy, heterocyclyl, or a protein reactive group;

$R^5$ represents alkyl or alkoxy; and $R^6$ represents a protein reactive group.

6 Claims, 7 Drawing Sheets

TRIPYRIDYL MACROCYCLIC COMPOUNDS

This application is a continuation of application Ser. No. 07/784,333, filed Oct. 29,1991, now U.S. Pat. No. 5,367,080 which is a continuation-in-part application of U.S. patent application Ser. No. 07/610,861 filed Nov. 8, 1990, now abandoned.

FIELD OF THE INVENTION

The present invention relates to novel immunoreagents and more particularly to targeting radioactive immunoreagents which find particular utility in therapeutic and diagnostic imaging compositions and methods. The present invention further relates to novel complexing agents.

BACKGROUND OF THE INVENTION

Prior to 1980, the targeting of tumor-bearing sites by radioimmunoglobulin had been demonstrated by a number of laboratories at different institutions (S. E. Order et al., "Use of Isotopic Immunoglobulin in Therapy," *Cancer Research* 40, 3001–7 (August 1980)). By 1980 it was demonstrated that tumors would concentrate radiolabeled-antibodies to tumor associated antigens and that radiolabeled reagents employed allowed both diagnostic imaging of tumors, e.g., by gamma camera imaging (radioimmunoscintigraphy) and positron tomography, and therapeutic treatment, i.e., reduction in tumor size by the targeting radioactive immunoreagent.

Early targeting with radiolabeled immunoreagents was carried out with radioactive-iodine. However, as noted by Scheinberg et al, "Tumor Imaging with Radioactive Metal Chelates Conjugated to Monoclonal Antibodies," *Science* 215, No. 19, 1511–13 (March 1982), iodine isotopes pose several problems, particularly with respect to scanning of tumor images. of the three commonly available isotopic forms, only $^{123}$I has the appropriate emission characteristics for imaging and a short enough half-life to be safely used diagnostically. The gamma radiation of $^{125}$I is too weak for imaging. $^{131}$I has often been used but is undesirable because of its long half-life and high energy gamma and cytotoxic beta radiations. $^{131}$I has also been used therapeutically for large tumors, but appears ineffective in the treatment of small tumors. Moreover, rapid metabolism of radioiodinated antibodies allows incorporation of the iodine into the thyroid and active excretion of the iodine by the stomach and urinary tract. This dispersion of the radioactive iodine hinders imaging of specific tumors since the tumors are hidden by background radiation.

In addition to tumor targeting with radioactive antibodies for diagnostic imaging and therapeutic treatment, similar targeting has been accomplished for diagnostic imaging of infarcts, specifically, myocardial infarcts, using antibodies to canine cardiac myosin (Khaw et al, "Myocardial Infarct Imaging of Antibodies to Canine Cardiac Myosin Indium—111—Diethylenetriamine Pentaacetic Acid," *Science* 209, 295–7 (July 1980), and for imaging atherosclerosis by targeting atherosclerotic plaques. The same disadvantages in the use of radioactive iodine exist for diagnostic infarct imaging as for tumor imaging and therapeutic treatment.

It is known that $^{111}$In can be complexed with 30 polyaminocarboxylic acids such as ethylene diaminetetraacetic acid (EDTA) and diethylenetriaminepentaacetic acid (DTPA). However, the covalent linkage of proteins (antibodies) to these complexing agents, accomplished by acylation with activated carbonyls, aromatic diazonium coupling, or bromoacetylation is inefficient, even though the isocyanatobenzyl derivatives described by Brechbiel et al "Synthesis of 1-(p-Isothiocyanatobenzyl)Derivatives of DTPA and EDTA. Antibody Labeling and Tumor Imaging Studies," *Inorg. Chem.* 25, 2772–81 (1986)) were created to facilitate covalent attachment of proteins with the complexing agents.

Recently, research efforts have been directed to improved antibodies (Ab's), e.g., monoclonal, specific antibodies for specific targeting, antibodies that complex or bind directly with radionuclides, preferred radionuclides and combinations thereof with antibodies and complexing agents. Some attempts have been made towards improving complexing agents.

Nonetheless, EDTA and especially DTPA and derivatives thereof have remained the prevalent complexing agents to covalently bind antibody and coordinately complex metallic radionuclides. However, the inadequacies of DTPA have been noted, for example, by Parker et al, "Implementation of Macrocycle Conjugated Antibodies for Tumor Targeting," *Pure and Appl. Chem.*, 61, No. 9, 1637–41 (1989) . . . "Conventionally the metal radionuclide has been complexed by an acyclic chelate (e.g. EDTA or DTPA) which is covalently linked to the antibody. None of the chelates is adequate because the metal tends to dissociate in vivo," . . . and by Cox et al, "Synthesis of a Kinetically Stable Yttrium-90 Labelled Macrocycle-Antibody Conjugate," *J. Chem. Soc., Chem. Commun.* 797–8 (1989) . . . "Yttrium-90 is an attractive isotope for therapy . . . but its clinical use will be very limited because of bone marrow toxicity, resulting from acid-promoted release of $^{90}$Y from an antibody linked chelate such as diethylenetriaminepentaacetic (DTPA)."

The attempts to develop improved complexing agents have provided materials which have their shortcomings. For example, Craig et al "Towards Tumor Imaging with Indium-111 Labelled Macrocycle-Antibody Conjugates," *J. Chem. Soc. Chem. Commun.*, 794–6 (1989) describe macrocyclic hexacoordinating ligands but state that "The limiting feature of this approach is that $^{111}$In labelling of the macrocycle is required before antibody conjugation. Indium binding by (4) is insufficiently fast at 37° C. for efficient radiolabeling . . . Other tribasic triazamacrocyclic ligands were screened therefore for their ability to bind indium rapidly under mild conditions (20° C., pH 5,<1 h), yet still form a kinetically stable complex in vivo . . . However, only (6) proved effective when the ligand concentration was 10 µM, and under these conditions a 96% radiolabeling yield was determined (30 min, pH 5, 20° C.)."

Nevertheless, thirty minutes is still unsatisfactory. It would be highly desirable to have complexing agents superior to EDTA and DTPA which would coordinately bind preferred radionuclides such as In, Y, Sc, Ga, Ge, etc. within a few minutes, i.e., in less than about 5 min, immediately prior to administration of the reagent to the patient, especially when a short-lived radionuclide must necessarily be generated from a longer-lived radionuclide at the time of treatment of the patient.

It should be noted that complexes of yttrium, a preferred radionuclide, tend to be less stable than those of indium (Mather et al, "Labelling Monoclonal Antibodies with Yttrium 90," *Eur. J. Nucl, Med.* 15, 307–312 (1989)) with respect to conventional complexes. Mather et al teach that biodistribution studies in cancer patients using radiolabeled antibodies have suggested that the in vivo stability of yttrium-labeled antibodies is not as great as their $^{111}$In-labelled counterparts and that these findings are supported by other recent publications in the field.

When chelating agents are covalently bonded to proteins (Ab's), the proteins usually are capable of accepting far more than one molecule of the chelating agent because they contain a host of amine and sulfhydryl groups through which the chelating agents are bound. It is often very important to determine how many chelating sites are bound to each protein molecule. The most convenient way to accomplish this is by spectrophotometric means. However, prior art chelating agents and chelates thereof have spectra that overlap with those of useful proteins, and an analytical determination of the number of chelating or chelated sites per molecule of protein cannot be made by spectroscopy since the overlapping spectra mask each other. It would thus be highly desirable to obtain chelating agents for conjugation to proteins whose spectra, and whose metal chelate spectra, do not overlap with that of the proteins to which the chelating agents are chemically bonded.

Another problem with some prior art compositions is that the chelator must be activated by a reducing agent before forming the radionuclide chelate. If the protein conjugates are to be formed prior to formation of the radionuclide chelate, then the reducing agent employed for activating the complexing agent can degrade the protein. For example, the preferred chelating agents currently used for complexing technetium (Tc) and rhenium (Re) complex to the metals via sulfur-containing groups which must be reduced with a reducing agent (dithiothreitol) to activate the chelator before forming the radionuclide chelate. If the protein conjugate containing disulfide bonds is formed prior to reduction, then the reducing agent can degrade the protein. It would be highly desirable to have chelating agents capable of forming conjugates with proteins before complexing with radionuclides, and particularly chelating agents for Tc and Re which do not require an activation step involving a reducing agent prior to complexation.

In summary, the various currently available radiolabeled antibodies and chelating agents employed for making immunoreactive conjugates by covalently bonding of a chelating agent to the immunoreactive protein, and radionuclide complexes thereof for use in diagnostic imaging and targeted therapeutics suffer from certain of the following disadvantages: 1) toxicity; 2) dispersion of the reagent due to rapid-metabolism; 3) inadequate emission characteristics; 4) inefficient covalent bonding with protein for conjugate 5 preparation; 5) slow complexation with metals; 6) unstable metal complexation, e.g., with respect to temperature, time or pH; 7) inability to form conjugates and store until metal complexation is desired; 8) inability to spectrophotometrically analyze the radionuclide complex reagent; and 9) inability to complex without activation steps that degrade protein.

SUMMARY OF THE INVENTION

We have discovered targeting radioactive immunoreagents which solve the problems of the prior art discussed above. The targeting radioactive immunoreagents of this invention comprise a metal radionuclide ion, a complexing agent which is a derivative of a pyridine, bipyridine, terpyridine, quaterpyridine, quinquepyridine, sexipyridine or phenanthroline, and an immunoreactive group covalently bonded through a protein reactive group to the complexing agent.

More particularly, in accordance with the invention, there is provided:

a targeting radioactive immunoreagent comprising a metal radionuclide ion, a complexing agent, and an immunoreactive group covalently bonded to the complexing agent, the completing agent having the structure

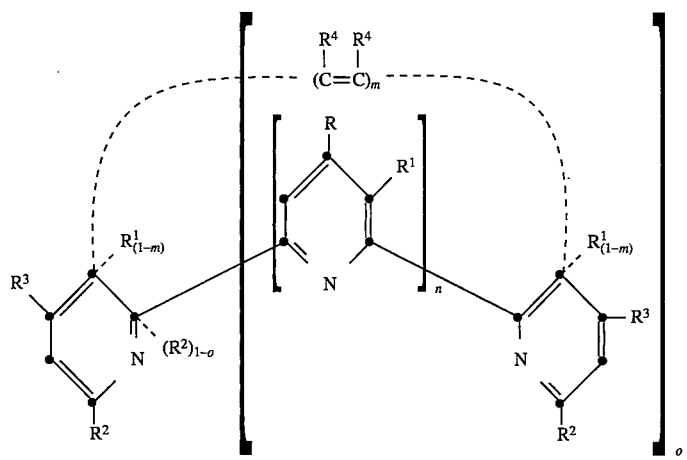

A-I wherein

R represents hydrogen, alkyl, alkoxy, alkylthio, alkylamino, alkylformamido, aryl, aryloxy, heterocyclyl or a protein reactive group;

$R^1$ represents hydrogen, alkyl, alkoxy, alkylthio, alkylamino, alkylformamido, aryl, aryloxy, heterocyclyl or a protein reactive group;

$R^2$ represents hydroxy, carboxy, hydroxyalkyl, carbonyliminodiacetic acid, methyleneiminodiacetic acid, methylenethioethyleneiminodiacetic acid, hydrazinylylidenediacetic acid, or a salt of such acids, or two $R^2$ groups, taken together, represent the atoms necessary to complete a macrocyclic ring structure containing at least one heteroatom coordinating site and at least one, preferably two alkylene groups forming part of the ring structure;

R³ represents hydrogen, alkyl, alkoxy, alkylthio, alkylamino, alkylformamido, aryl, aryloxy, heterocyclyl or a protein reactive group;

R⁴ represents hydrogen or a protein reactive group;

n is 0 to 4 o is 0 or 1 m is 0 or 1;

provided that at least one of n and m is 0 and at least one of R, R¹ R³ and R⁴ is a protein reactive group The pyridines have the structure

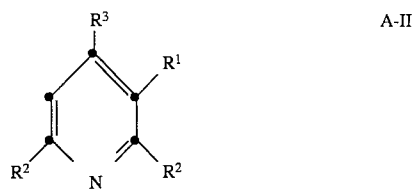

wherein R¹ R² and R³ are as defined above

The bipyridines, terpyridines, quaterpyridines, quinquepyridines and sexipyridines have the structure

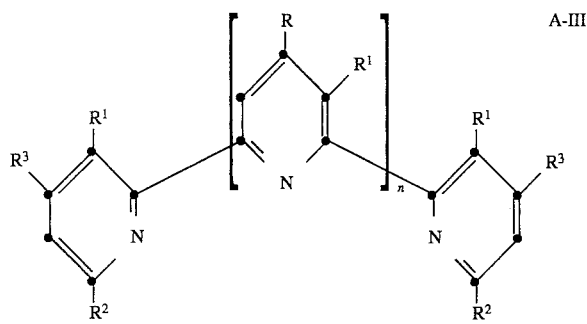

wherein R, R¹ R² and R³ are as defined above and n is 0, 1, 2, 3 or 4.

The phenanthrolines have the structure

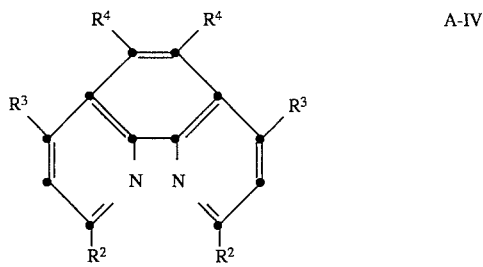

wherein R², R³ and R⁴ are as defined above.

This invention provides novel terpyridines, preferably having the structure A-III above wherein n=1, R is

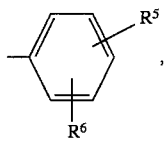

R⁵ is alkoxy or alkyl, and R⁶ is a protein reactive group.

This invention further provides novel phenanthrolines preferably having the structure A-IV above wherein at least one R⁴ is a protein reactive group.

This invention also provides therapeutic and diagnostic compositions comprising the above-described targeting radioactive immunoreagent.

This invention further provides a method for diagnostic imaging a site in a patient comprising a) administering to the patient an effective amount of the above-described radioactive immunoreagent capable of targeting the site, and b) imagewise activating a radiation-sensitive element or device, such as, for example, a film or electronic sensor, with the radiation emitted from the targeted site.

A method for treating disease sites in a patient according to this invention comprises administering to the patient or a specimen from the patient an effective amount of a therapeutic composition comprising the above-described radioactive immunoreagent capable of targeting the site and a pharmaceutically acceptable carrier therefor.

It is an advantageous feature of this invention that the described targeting radioactive immunoreagents exhibit lower toxicity, e.g., compared to other radioactive yttrium chelators.

It is an advantageous feature that the targeting immunoreagents of this invention are not rapidly metabolized and do not deleteriously disperse.

It is another advantageous feature that the described complexes efficiently form covalent bonds with proteins and other biological molecules.

Yet another advantageous feature of this invention is that the described immunoreagents exhibit good emission characteristics and are readily subject to spectrophotometric analysis.

Additionally, protein conjugates of the complexing agents can be formed and stored until metal complexation is desired and complexation can be accomplished without activation steps that degrade protein.

Moreover, the complexing agents rapidly complex with metals, and the resulting chelates exhibit excellent stability with respect to time, temperature and pH.

Other advantageous features of this invention will become readily apparent upon reference to the following description of the preferred embodiments, when read in light of the accompanying drawings.

DESCRIPTION OF PREFERRED EMBODIMENTS

Figure 1:
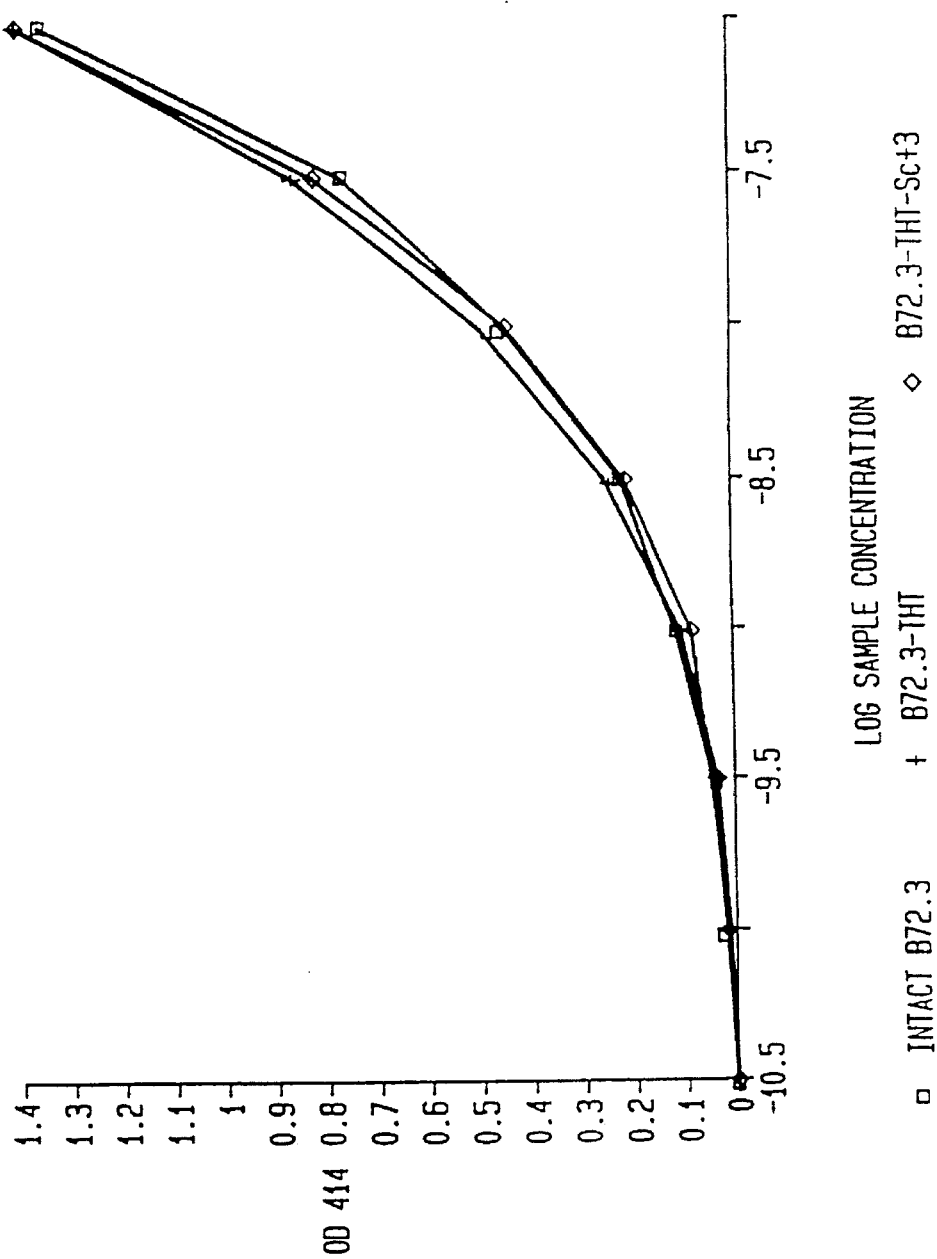
FIG. 1 depicts immunocompetency assays of B72.3-THT-Sc⁺⁺⁺, a radioactive immunoreagent of this invention, a B72.3-THT conjugate and unmodified B72.3.

The description which follows primarily 5 concerns usage of the targeting radioactive immunoreagents in therapeutic and diagnostic imaging compositions and methods. In addition, the targeting radioactive immunoreagents are useful as diagnostic reagents, for example, radioimmunoelectrophoresis reagents.

The immunoreagents of this invention comprise a metal radionuclide ion, a complexing agent, and an immunoreactive group covalently bonded to the complexing agent through a protein reactive group.

The complexing agent is a derivative of a pyridine, bipyridine, terpyridine, quaterpyridine, quinquepyridine, sexipyridine or phenanthroline, preferably having the structural formula A-I recited in the Summary above.

Each R in formula A-I independently is hydrogen; straight or branched alkyl, preferably containing from 1 to about 20 carbon atoms such as methyl, ethyl, propyl, isopropyl, butyl, s-butyl, t-butyl, 2-ethylhexyl, decyl, hexadecyl, octadecyl, etc.; alkoxy, the alkyl portion of which contains from 1 to about 20 carbon atoms as described for R above; alkylthio, the alkyl portion of which contains from 1 to about 20 carbon atoms as described for R above; alkylamino, the alkyl portion of which contains from 1 to about 20 carbon atoms as described for R above; alkylformamido, the alkyl portion of which contains from 1 to about 20 carbon atoms as described for R above; substituted or unsubstituted aryl, preferably containing from about 6 to 20 carbon atoms such as phenyl, naphthyl, phenanthryl, nitrophenyl, 10 hydroxyphenyl, aminophenyl, hexadecylaminophenyl, octadecylaminophenyl, tolyl, xylyl, methoxyphenyl, 3-amino-4-methoxyphenyl, 4-methoxy-3-(N-methylhydrazinothioformamido)phenyl, 3-isocyanato-4-methoxyphenyl, 3-isothiocyanato-4-methoxyphenyl, methylthiophenyl, carboxyphenyl and alkylaryl such as alkylphenyl, the alkyl portion of which contains from 1 to about 20 carbon atoms as described for R above; aryloxy, the aryl portion of which contains from 6 to about 20 carbon atoms as described for R above; a substituted or unsubstituted heterocyclyl, preferably containing 5 to 6 nuclear carbon and heteroatoms such as N, S, P or O, such as pyridyl, methylpyridyl, nitropyridyl, methoxypyridyl, oxazolyl, imidazolyl, pyrazolyl and quinolyl; or a protein reactive group. In especially preferred embodiments, R is a 4-alkoxy-3-aminophenyl or a 4-alkoxy-3-isothiocyanato phenyl group.

Each $R^1$ independently is selected from the groups specified for R. $R^1$ preferably represents hydrogen or a protein reactive group.

Each $R^2$ is independently selected from hydroxy; carboxy; hydroxyalkyl, the alkyl portion of which preferably contains from 1 to 4 carbon atoms, such as hydroxymethyl; carbonyliminodiacetic acid [—CON(CH$_2$COOH)$_2$]; methyleneiminodiacetic acid [—CH$_2$N(CH$_2$COOH)$_2$]; methylenethioethyleneiminodiacetic acid [—CH$_2$SCH$_2$CH$_2$N(CH$_2$COOH)$_2$]; hydrazinylylidenediacetic acid, such as 1-hydrazinyl-2-ylidenediacetic acid [—NHN (CH$_2$COOH)$_2$] and 1-methyl-1-hydrazinyl-2-ylidenediacetic acid [—N(CH$_3$)N(CH$_2$COOH)$_2$]; and 2,6-dicarboxy piperidino or the salts of such acids, including, for example, metal salts of such acids formed from such metals as Na, K, Li, etc., and ammonium salts such as ammonium, tetraethylammonium, and tetramethylammonium salts. Alternatively, the two $R^2$ groups, taken together, represent the atoms necessary to complete a macrocyclic ring structure containing (a) at least one heteroatom coordinating site for ions, and (b) at least one, preferably two alkylene groups forming part of the ring structure. The macrocyclic ring-forming groups can be a heteroatom group substituted alkylene such as 2,2-bis(ethoxycarbonyl)- 1,3-propylene; or heteroatom-containing groups such as oxybis (alkylene) such as oxybis (ethylene), oxybis (ethyleneoxymethylene), oxybis (ethyleneoxyethylene); akyleneoxyalkyleneoxyalkylene, such as methyleneoxyethyleneoxymethylene; arylenedi(oxyalkylene), such as 1,4-dimethyl-5,6-phenylenebis(oxymethylene); 2,6-pyridylenebis(methyleneoxymethylene); 2-methoxy-5-methyl-1,3-phenylenebis(methyleneoxymethylene) and 1,10-phenanthrolin-2,9-ylenebis(methyleneoxymethylene); carboxymethyliminobis(trimethylenecarboxymethyliminomethylene) [—CH$_2$N (CH$_2$COOH)(CH$_2$)$_3$N(CH$_2$COOH)— (CH$_2$)$_3$N(CH$_2$COOH) CH$_2$—]; carboxymethylthioethyliminobis(trimethylene carboxymethylthioethyliminomethylene)[—CH$_2$N (CH$_2$CH$_2$SCH$_2$COOH)$_2$— (CH$_2$)$_3$N(CH$_2$—CH$_2$SCH$_2$COOH)$_2$— (CH$_2$)$_3$N(CH$_2$CH$_2$SCH$_2$COOH)—CH$_2$—]; carboxymethyliminobis(ethylenecarboxymethyliminomethylene)[—CH$_2$N (CH$_2$COOH)CH$_2$CH$_2$N(CH$_2$COOH)CH$_2$CH$_2$N(CH$_2$COOH) CH$_2$—]; carboxymethylthioethyliminobis(ethylenecarboxymethylthioethyliminomethylene) [—CH$_2$N(CH$_2$CH$_2$SCH$_2$COOH)CH$_2$CH$_2$N(CH$_2$CH$_2$SCH$_2$COOH)CH$_2$CH$_2$N(CH$_2$CH$_2$SCH$_2$COOH)— CH$_2$—]; ethylenebis(carboxymethyliminomethylene [—CH$_2$N(CH$_2$COOH)CH$_2$CH$_2$N(CH$_2$COOH)CH$_2$—]; carboxymethyliminobis(methylene) [—CH$_2$N (CH$_2$COOH)CH$_2$—]; or the salts of the exemplified carboxylic acid containing groups, including, for example, the metal and ammonium salts of such acids as described for $R^2$ above. In especially preferred embodiments, $R^2$ is methyleneiminodiacetic acid or a salt thereof.

Each $R^3$ independently is selected from the groups specified for R. $R^3$ preferably represents hydrogen.

Each $R^4$ is independently selected from hydrogen or a protein reactive group.

In formula A-I above, n is 0, 1, 2, 3 or 4; m is 0 or 1; and o is 0 or 1; provided that at least one of n and m is 0.

At least one of the R, $R^1$ $R^3$ and $R^4$ groups present is a protein reactive group. Preferably, no more than one of the R, $R^1$ $R^3$ and $R^4$ groups on each aromatic ring is a protein reactive group. Most preferably, only one of the R, $R^1$ $R^3$ and $R^4$ groups per molecule is a protein reactive group, By "protein reactive group" it is meant any group which can react with any functional groups typically found on proteins. However, it is specifically contemplated that the protein reactive group can be conjugated to nonprotein biomolecules. Thus the protein reactive groups useful in the practice of this invention include those groups which can react with any biological molecule containing an immunoreactive group, whether or not the biological molecule is a protein to form a linking group between the complexing agent and the immunoreactive group.

Preferred protein reactive groups can be selected from but are not limited to: ( 1 ) A group that will react directly with the amine or sulfhydryl groups on the protein or biological molecule containing the immunoreactive group, for example, active halogen containing groups including, for example, chloromethylphenyl groups and chloroacetyl [Cl—CH$_2$CO—] groups, activated 2-leaving group substituted ethylsulfonyl and ethylcarbonyl groups such as 2-chloroethylsulfonyl and 2-chloroethylcarbonyl; vinylsulfonyl; vinylcarbonyl; epoxy; isocyanato; isothiocyanato; aldehyde; aziridine; succinimidoxycarbonyl; activated acyl groups such as carboxylic acid halides; mixed anhydrides and the like; and other groups known to be useful in conventional photographic gelatin hardening agents. (2) A group that can react readily with modified proteins or biological molecules containing the immunoreactive group, i.e., proteins or biological molecules containing the immunoreactive group modified to contain reactive groups such as those mentioned in (1) above, for example, by oxidation of the protein to an aldehyde or a carboxylic acid, in which case the "protein reactive group" can be selected from amino, alkylamino, arylamino, hydrazino, alkylhydrazino, arylhydrazino, carbazido, semicarbazido, thiocarbazido, thiosemicarbazido, sulfhydryl, sulfhydrylalkyl, sulfhydrylaryl, hydroxy, carboxy, carboxyalkyl and carboxyaryl. The alkyl portions of the protein reactive group can contain from 1 to about 20 carbon atoms as described for R above. The aryl portions of the protein reactive group can contain from about 6 to about 20 carbon atoms as described for R above. (3) A group that can be linked to the protein or biological molecule containing the immunoreactive group, or to the modified protein as noted in (1) and (2) above by use of a crosslinking agent. Certain useful crosslinking agents, such as, for example, difunctional gelatin hardeners, bisepoxides and bisisocyanates become a part of, i.e., a linking group in, the protein-complexing agent conjugate during the crosslinking reaction. Other useful crosslinking agents, however, facilitate the crosslinking, for example, as consumable catalysts, and are not present in the final conjugate. Examples of such crosslinking agents are carbodiimide and carbamoylonium crosslinking agents as disclosed in U.S. Pat. No. 4,421,847, the disclosure of which is hereby incorporated by reference in its entirety, and the dication ethers of U.S. Pat. No. 4,877,724, the disclosure of which is hereby incorporated by reference in its entirety. With these crosslinking agents, one of the reactants must have a carboxyl group and the other an amine or sulfhydryl group. The crosslinking agent first reacts selectively with the carboxyl group, then is split out during reaction of the "activated" carboxyl group with an amine to form an amide linkage between the protein and metal complexing agents having the structure A-I above, this covalently bonding the two moieties. An advantage of this approach is that crosslinking of like molecules, e.g., proteins with proteins or complexing agents with complexing agents is avoided, whereas the reaction of difunctional crosslinking agents is nonselective and unwanted crosslinked molecules are obtained. Especially preferred protein reactive groups include amino and isothiocyanato.

Especially preferred complexing agents include species 1–58 set forth below.

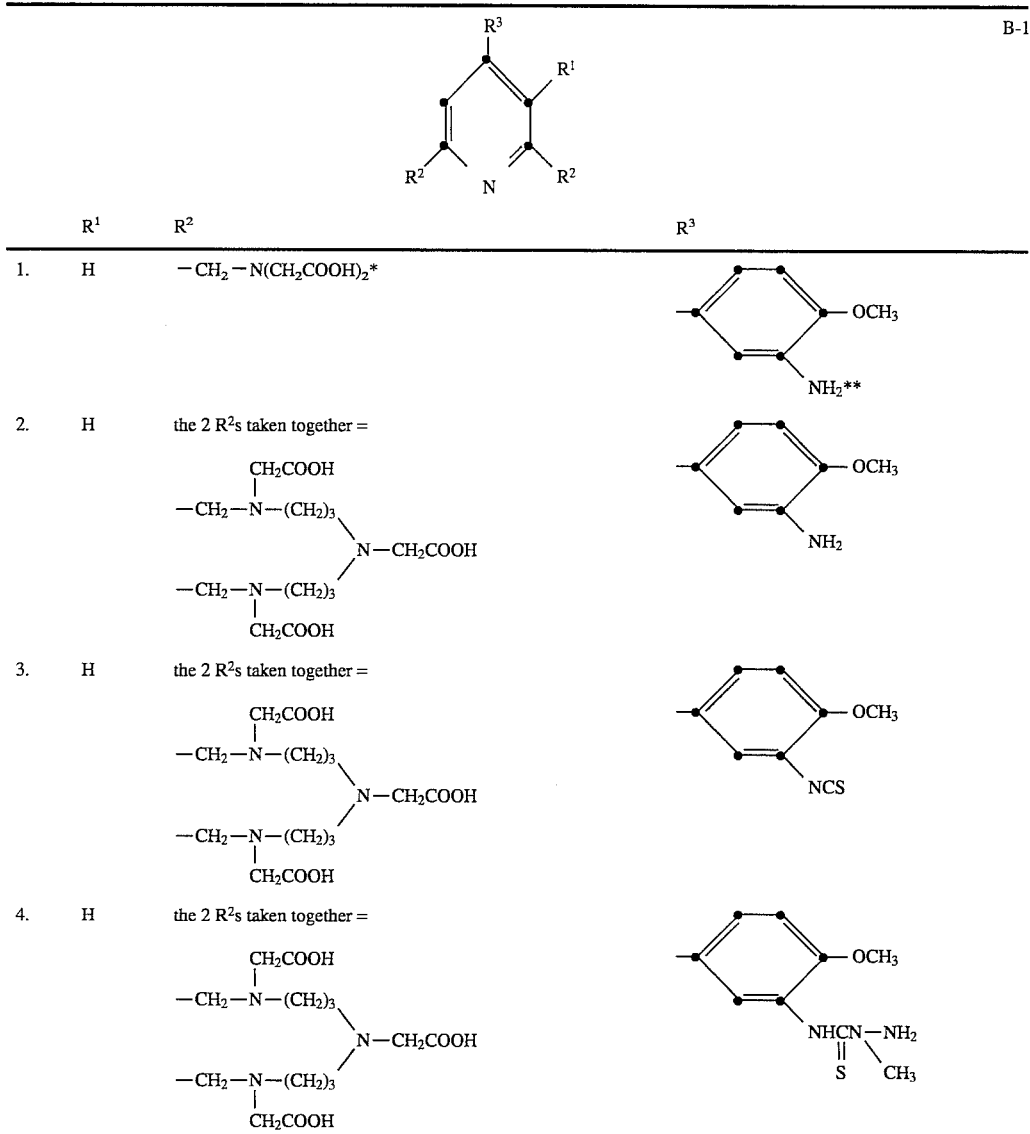

-continued

| | | | |
|---|---|---|---|
| 5. | H | the 2 R²s taken together = <br><br> −CH₂−N(CH₂CH₂SCH₂COOH)−(CH₂)₃ <br> N−CH₂CH₂SCH₂COOH <br> −CH₂−N(CH₂CH₂SCH₂COOH)−(CH₂)₃ | 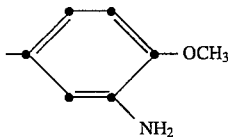 4-OCH₃, 3-NH₂ phenyl |
| 6. | H | the 2 R²s taken together = <br><br> −CH₂−N(CH₂CH₂SCH₂COOH)−(CH₂)₃ <br> N−CH₂CH₂SCH₂COOH <br> −CH₂−N(CH₂CH₂SCH₂COOH)−(CH₂)₃ | 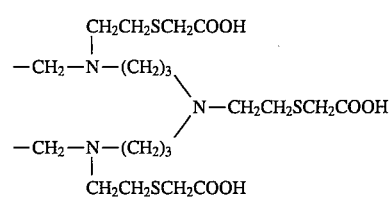 4-OCH₃, 3-NCS phenyl |
| 7. | H | the 2 R²s taken together = <br><br> −CH₂−N(CH₂CH₂SCH₂COOH)−(CH₂)₃ <br> N−CH₂CH₂SCH₂COOH <br> −CH₂−N(CH₂CH₂SCH₂COOH)−(CH₂)₃ | 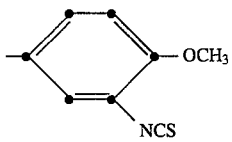 4-OCH₃, 3-NHC(=S)−N(CH₃)−NH₂ phenyl |

B-2

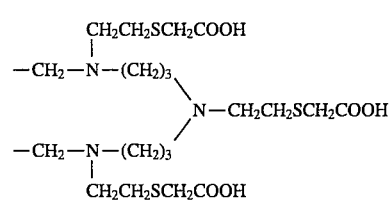

| | R | R² |
|---|---|---|
| 8. | 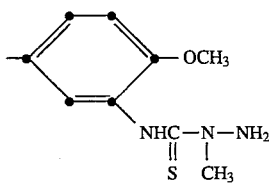 4-OCH₃, 3-NH₂ phenyl | −CH₂−N(CH₂COOH)₂ |
| 9. | 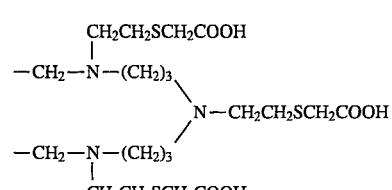 4-OCH₃, 3-NCS phenyl | −CH₂−N(CH₂COOH)₂ |
| 10. | 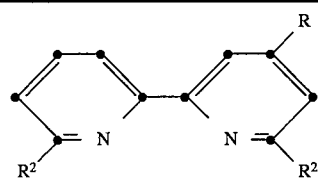 4-OCH₃, 3-NHC(=S)−N(CH₃)−NH₂ phenyl | −CH₂−N(CH₂COOH)₂ |

-continued
| | | |
|---|---|---|
| 11. | 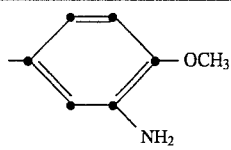 | the 2 R²s taken together = 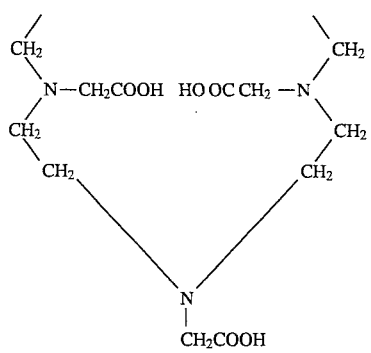 |
| 12. | 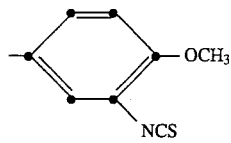 | the 2 R²s taken together = 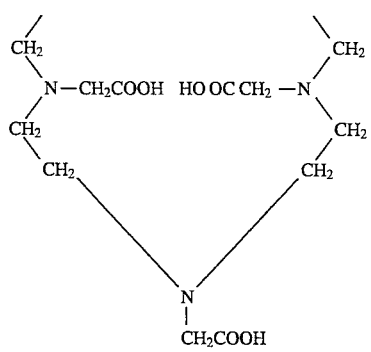 |
| 13. | 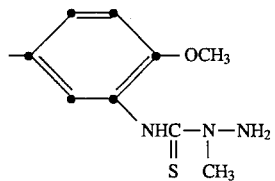 | the 2 R²s taken together = 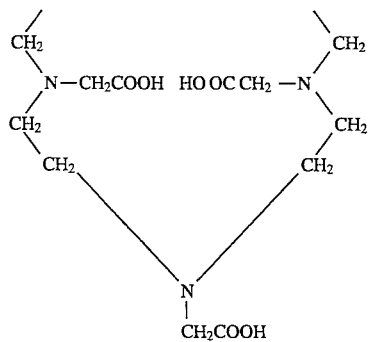 |
| 14. | 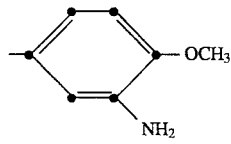 | the 2 R²s taken together = 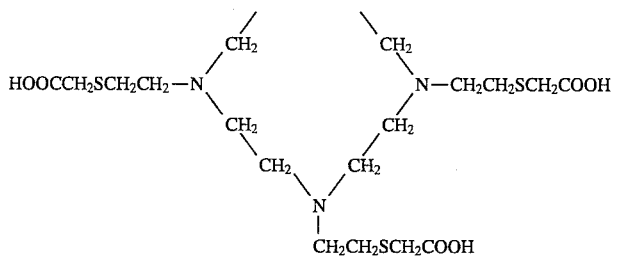 |

-continued
| | | |
|---|---|---|
| 15. 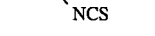 | the 2 R²s taken together = HOOCCH₂SCH₂CH₂—N(CH₂CH₂)₂N—CH₂CH₂SCH₂COOH with bridging N—CH₂CH₂SCH₂COOH | |
| 16. 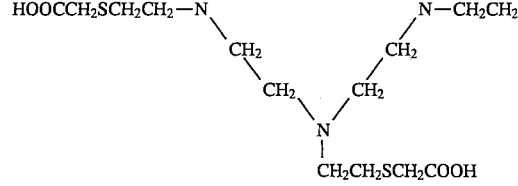 | the 2 R²s taken together = HOOCCH₂SCH₂CH₂—N(CH₂CH₂)₂N—CH₂CH₂SCH₂COOH with bridging N—CH₂CH₂SCH₂COOH | |
| 17. 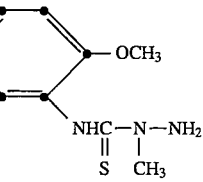 | —CH₂SCH₂CH₂N(CH₂COOH)₂ | |
| 18. 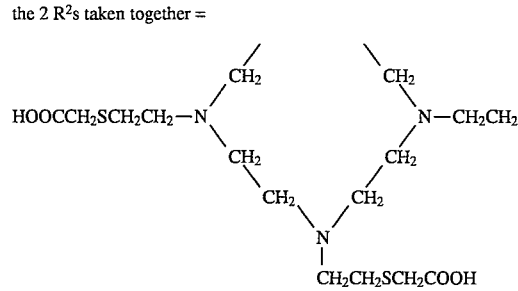 | —CH₂SCH₂CH₂N(CH₂COOH)₂ | |
| 19.  | —CH₂SCH₂CH₂N(CH₂COOH)₂ | |
B-3
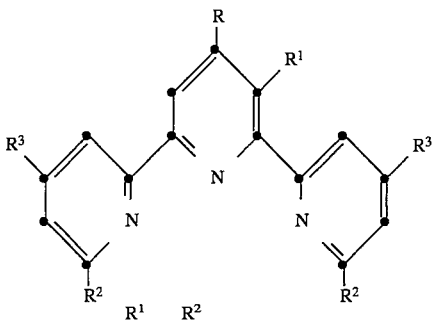
| | R | R¹ | R² | R³ |
|---|---|---|---|---|
| 20. |  | H | —N(CH₃)N(CH₂COOH)₂ | H |

-continued

| # | Structure | | | |
|---|---|---|---|---|
| 21. | benzene ring with -OCH₃ and -NH₂ substituents | H | -CH₂N(CH₂COOH)₂ | H |
| 22. | benzene ring with -OCH₃ and -NCS substituents | H | -N(CH₃)N(CH₂COOH)₂ | H |
| 23. | benzene ring with -OCH₃ and -NHC(=S)N(CH₃)NH₂ substituents | H | -N(CH₃)N(CH₂COOH)₂ | H |
| 24. | benzene ring with -OCH₃ and -NCS substituents | H | -CH₂N(CH₂COOH)₂ | H |
| 25. | benzene ring with -OCH₃ and -NHC(=S)N(CH₃)NH₂ substituents | H | -CH₂N(CH₂COOH)₂ | H |
| 26. | benzene ring with -OCH₃ and -NH₂ substituents | H | the 2 R²s taken together = $-CH_2-N(CH_2COOH)-CH_2CH_2-N(CH_2COOH)-CH_2CH_2-N(CH_2COOH)-CH_2-$ | H |
| 27. | benzene ring with -OCH₃ and -NCS substituents | H | the 2 R²s taken together = $-CH_2-N(CH_2COOH)-CH_2CH_2-N(CH_2COOH)-CH_2CH_2-N(CH_2COOH)-CH_2-$ | H |
| 28. | benzene ring with -OCH₃ and -NHC(=S)-N(CH₃)-NH₂ substituents | H | the 2 R²s taken together = $CH_2-N(CH_2COOH)-CH_2CH_2-N(CH_2COOH)-CH_2CH_2-N(CH_2COOH)-CH_2-$ | H |

5,523,402

-continued

| # | | | | |
|---|---|---|---|---|
| 29. | ![benzene with OCH3 and NH2] | H | the 2 R²s taken together =<br><br>$-CH_2-N(CH_2CH_2SCH_2COOH)-CH_2-CH_2$<br>$\qquad\qquad\qquad\qquad\qquad\qquad\qquad\qquad N-CH_2CH_2SCH_2COOH$<br>$-CH_2-N(CH_2CH_2SCH_2COOH)-CH_2-CH_2$ | H |
| 30. | ![benzene with OCH3 and NCS] | H | the 2 R²s taken together =<br><br>$-CH_2-N(CH_2CH_2SCH_2COOH)-CH_2-CH_2$<br>$\qquad\qquad\qquad\qquad\qquad\qquad\qquad\qquad N-CH_2CH_2SCH_2COOH$<br>$-CH_2-N(CH_2CH_2SCH_2COOH)-CH_2-CH_2$ | H |
| 31. | ![benzene with OCH3 and NHC(=S)-N(CH3)-NH2] | H | the 2 R²s taken together =<br><br>$-CH_2-N(CH_2CH_2SCH_2COOH)-CH_2-CH_2$<br>$\qquad\qquad\qquad\qquad\qquad\qquad\qquad\qquad N-CH_2CH_2SCH_2COOH$<br>$-CH_2-N(CH_2CH_2SCH_2COOH)-CH_2-CH_2$ | H |
| 32. | ![benzene with OCH3 and NH2] | H | the 2 R s taken together =<br><br>$N(CH_3)N(CH_2CO_2H)-CH_2-CH_2-N(CH_3)N(CH_2CO_2H)$ | H |

B-4

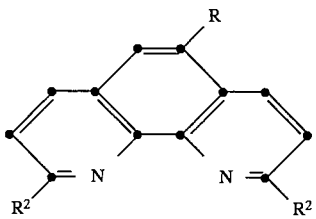

| | R | R² |
|---|---|---|
| 33. | $-NH_2$ | $-CH_2-N(CH_2COOH)_2$ |
| 34. | $-NCS$ | $-CH_2-N(CH_2COOH)_2$ |
| 35. | $-NHCN(CH_3)-NH_2$<br>$\quad\;\;\|\|$<br>$\quad\;\;S$ | $-CH_2-N(CH_2COOH)_2$ |

| | | |
|---|---|---|
| 36. | $-NH_2$ | the 2 $R^2$s taken together = 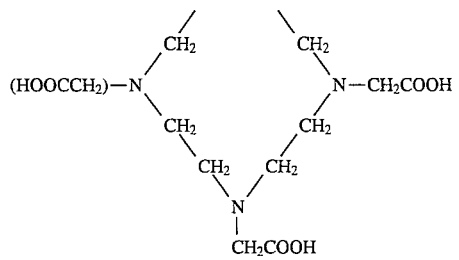 |
| 37. | $-NCS$ | the 2 $R^2$s taken together = 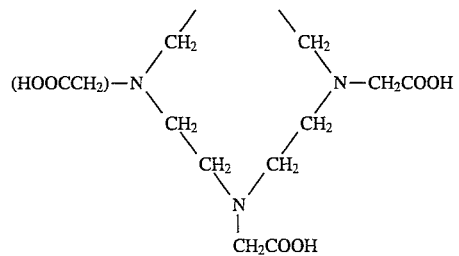 |
| 38. | 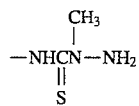 | the 2 $R^2$s taken together = 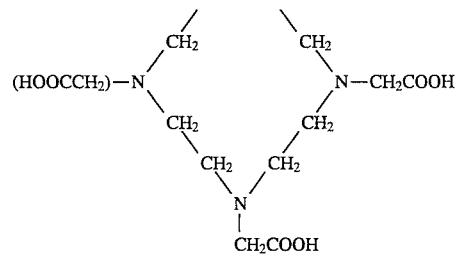 |
| 39. | $-NH_2$ | the 2 $R^2$s taken together = 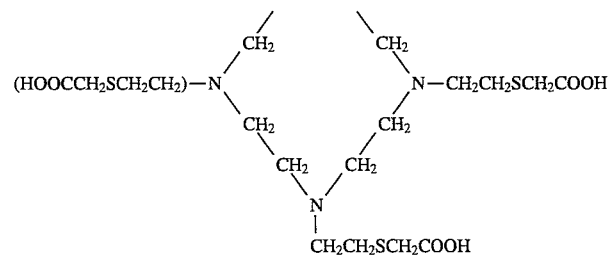 |
| 40. | $-NCS$ | the 2 $R^2$s taken together = 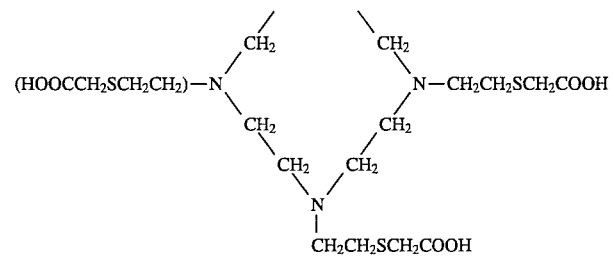 |

| | | | |
|---|---|---|---|
| 41. | 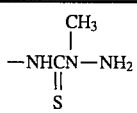 | the 2 R²s taken together = | |
| | | 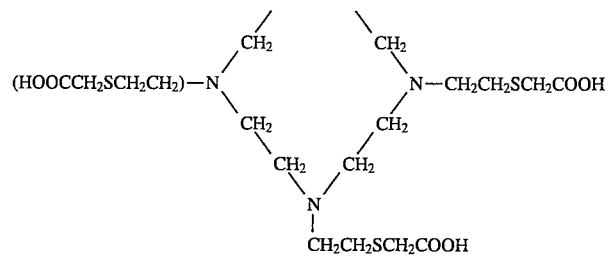 | |
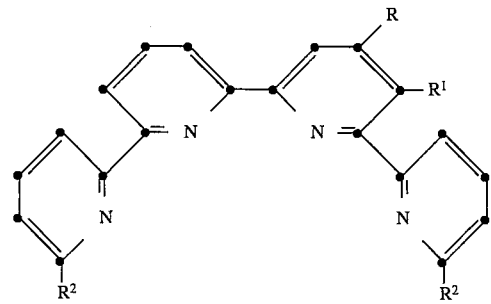 B-5
| | R | R¹ | R² |
|---|---|---|---|
| 42. | 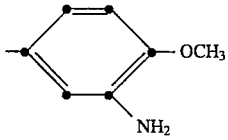 | H | $-CH_2-N(CH_2COOH)_2$ |
| 43. |  | H | $-CH_2-N(CH_2COOH)_2$ |
| 44. | 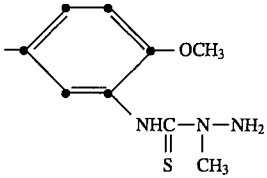 | H | $-CH_2-N(CH_2COOH)_2$ |
| 45. | 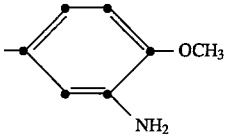 | H | the 2 R²s taken together = 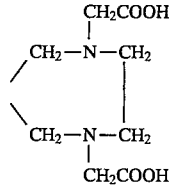 |
| 46. | 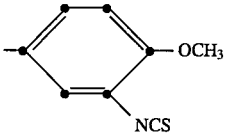 | H | the 2 R²s taken together = 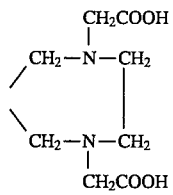 |

-continued
| 47. | 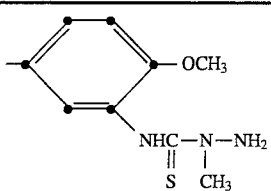 | H | the 2 R²s taken together =<br>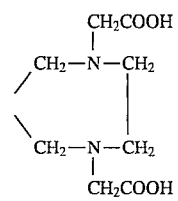 |
| --- | --- | --- | --- |
| 48. | 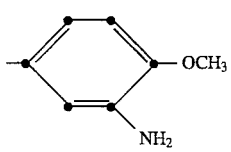 | H | the 2 R²s taken together =<br>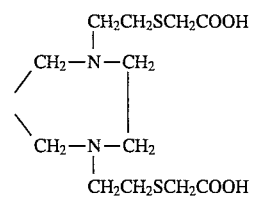 |
| 49. | 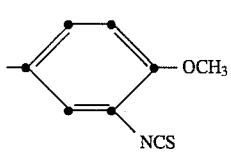 | H | the 2 R²s taken together =<br>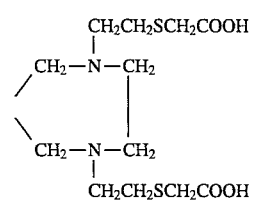 |
| 50. | 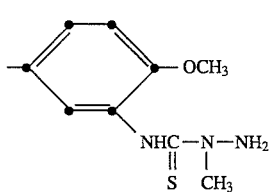 | H | the 2 R²s taken together =<br>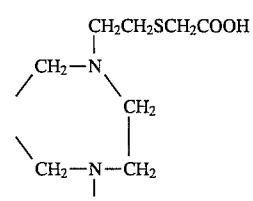 |
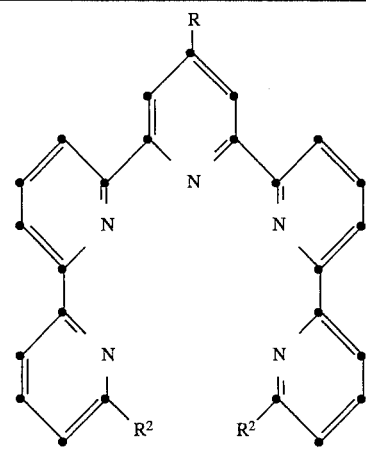
B-6
| | R | R² |
| --- | --- | --- |
| 51. | 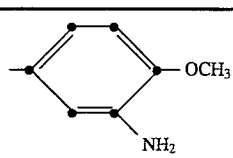 | $-CH_2-N(CH_2COOH)_2$ |

| | | |
|---|---|---|
| 52. | 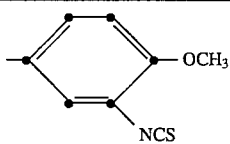 | $-CH_2-N(CH_2COOH)_2$ |
| 53. | 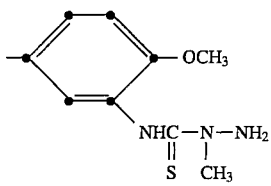 | $-CH_2-N(CH_2COOH)_2$ |
| 54. | 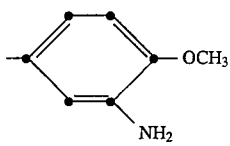 | the 2 $R^2$s taken together = 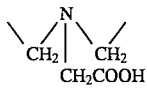 |
| 55. | 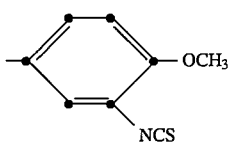 | the 2 $R^2$s taken together = 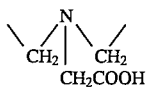 |
| 56. | 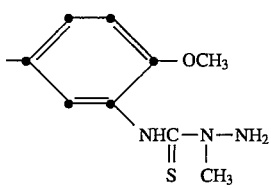 | the 2 $R^2$s taken together = 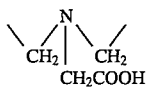 |
| 57. | 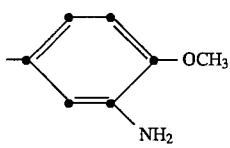 | the 2 $R^2$s taken together = 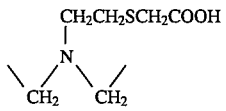 |
| 58. | 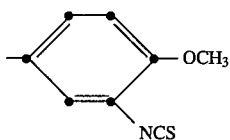 | the 2 $R^2$s taken together = 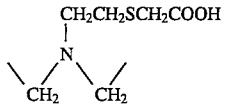 |
| 59. | 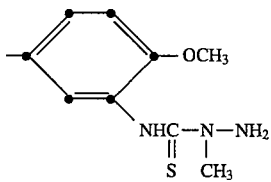 | the 2 $R^2$s taken together = 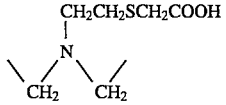 |

*The hydrogen in all carboxy (—COOH) groups can be replaced by a metal or ammonium cation.
**All $NH_2$ groups can be replaced by NCS or $NHCSN(CH_3)NH_2$ Preferred classes of complexing agents for use herein include terpyridines represented structure A-III above and phenanchrolines represented by structure A-IV above. A particularly preferred class of complexing agents has the structure A-III above wherein n=1 and R is a substituted phenyl containing an alkyl or alkoxy substituent and a protein reactive group- Representative preferred species of complexing agents include compounds 20–32 depicted above. The currently most preferred complexing agent is TMT (compound 21).

This invention provides novel terpyridines having the structure A-III set forth in the summary above wherein n=1 and R is

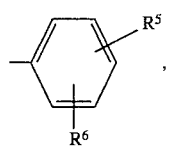

$R^5$ is alkoxy or alkyl, and $R^6$ is a protein reactive group. $R^5$ is alkyl, preferably containing from 1 to about 20, more preferably from 1 to 8 carbon atoms, such as methyl, ethyl and the like; or alkoxy, the alkyl protein which contain from 1to about 20, more preferably from 1 to 8 carbon atoms, such as methoxy, ethoxy and the like. $R^6$ is a protein reactive group as described above. Preferred protein reactive groups include amino, alkylamino, arylamino, carbazido, semicarbazido, thiosemicarbazido, thiocarbazido, isocyanato and isothiocyanato. Especially preferred protein reactive groups include amino, isothiocyanato, and semicarbazido. Especially preferred species include TMT (compound 21) and compound 20 (THT) depicted above.

Preferred phenanthrolines according to this invention have the structure A-IV above wherein least one $R^4$ is a protein reactive group. Preferred protein reactive groups include those specified for $R^6$ above.

The polypyridine and phenanthroline complexing agents having metal complexing sites, e.g., heteroatoms and iminodiacetate groups can be prepared by techniques known in the art. Suitable reaction schemes are illustrated in U.S. Pat. No. 4,837,169 and U.S. Pat. No. 4,859,777, the disclosures of which are hereby incorporated by reference.

The preparation of currently preferred compounds of this invention, namely: 4'-(3-amino-4-methoxyphenyl)-6,6"-bis(N',N'-dicarboxymethyl-N-methylhydrazino)- 2,2': 6',2"-terpyridine, tetrasodium salt (THT) and 4'-(3-amino-4-methoxyphenol)- 6,6"-bis [N,N-di-(carboxymethyl)aminomethyl]-2,2': 6',2"-terpyridine, tetrasodium salt (TMT) are illustrated in the following Reaction Scheme I:

Reaction Scheme I

Synthesis of THT and TMT

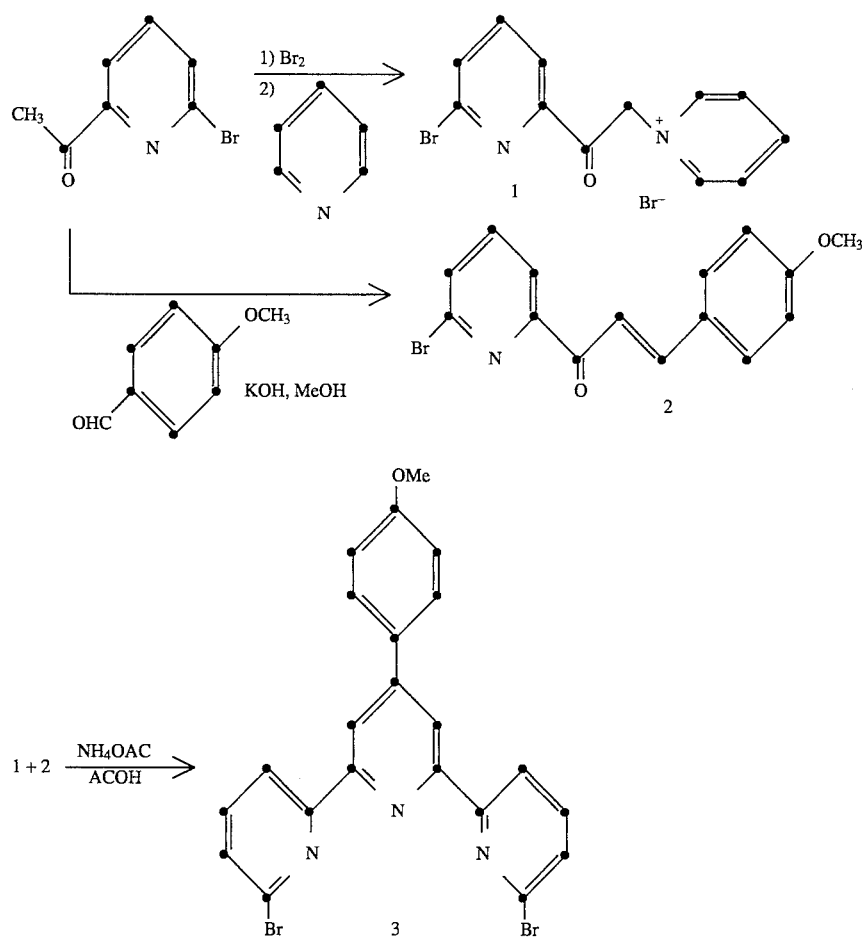

-continued
Reaction Scheme I
THT Synthesis
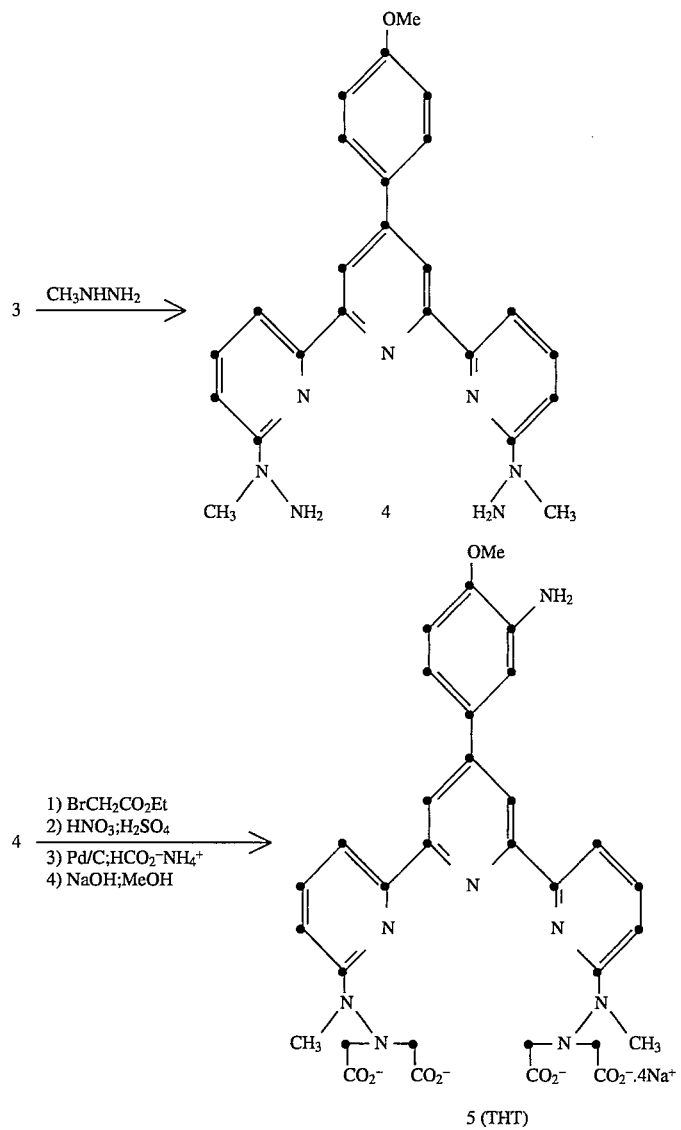
5 (THT)

-continued
Reaction Scheme I

TMT Synthesis

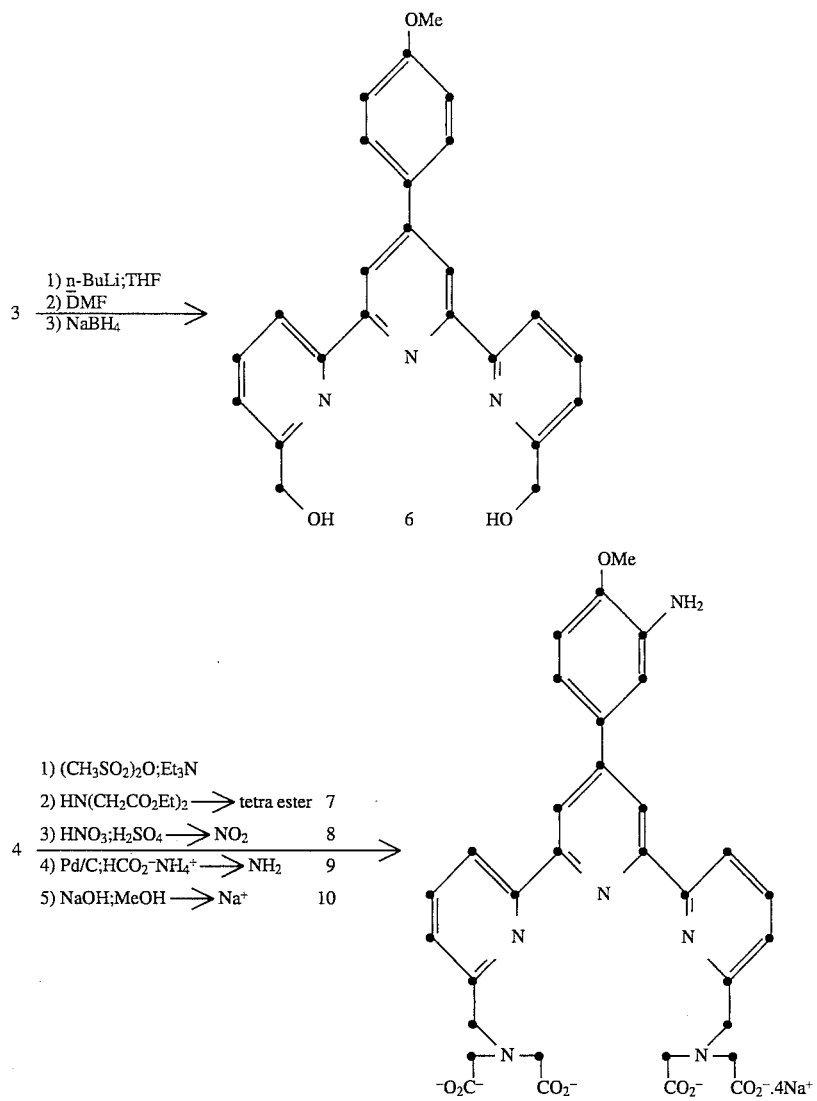

10 (TMT)

The addition to these molecules of the requisite protein reactive group described above can be accomplished by conventional chemical reactions. For example, amine groups can be added to polypyridines and phenanthrolines by nitration followed by reduction of the nitro groups to amines. If desired, the amine groups can be readily converted to isocyanate groups by reaction with phosgene to produce the carbamoyl chloride which, upon heating, releases HCl to produce the isocyanate. Carboxy groups can be added by treatment of the amine-substituted polypyridines and phenanthrolines with agents such as glutaric anhydride, followed by suitable selective activation of the carboxyl functionality. Cyclic acetal protected aldehydes can be carried through the reaction sequence necessary to synthesize the polypyridine chelators, and then deprotected before protein conjugation.

The class of terpyridines conforming to Structure A-III above and containing a phenyl group substituted with an alkyl or alkoxy substituent and a protein reactive group is particularly advantageous from a synthetic standpoint. The presence of the alkyl or alkoxy group on the dibrominated starting material (3) provides enhanced solubility in THF which is a preferred solvent used in the preparation of the intermediate diol (6).

The novel terpyridines and phenanthrolines of this invention can be prepared according to the above described synthetic techniques. Additional illustrative preparations are set forth in the examples which follow.

The targeting radioactive immunoreagent of this invention includes a radionuclide ion. The radionuclide ion can be selected, for example, from Sc, Fe, Pb, Ga, Y, Bi, Mn, Cu, Cr, Zn, Ge, Mo, Tc, Ru, In, Sn, Sm, Sb, W, Re, Po, Ta and Tl ions. Preferred radionuclides include $^{44}Sc^{+++}$, $^{64,67}Cu^{++}$, $^{111}In^{+++}$, $^{212}Pb^{++}$, $^{68}Ga^{++}$, $^{90}Y^{+++}$ and $^{212}Bi^{+++}$ ions. Of these, the most preferred are $^{90}Y^{+++}$ ions.

The metal radionuclide ion and the complexing agent are easily complexed by merely mixing an aqueous solution of the complexing agent with a metal radionuclide salt in an aqueous solution preferably having a pH of 4 to 11. The salt can be any water soluble salt of the metal such as halogen salts. The chelate is generally prepared in aqueous solution at a pH of between 5 and 9 and preferably 6 to 8. The complex optionally is mixed with buffers such as acetate, phosphate and borate to produce the optimum pH.

The targeting immunoreagent of this invention includes an immunoreactive group covalently bonded to the complexing agent. The targeting immunoreagent thus comprises a conjugate of a complex having the structure A-I above and the immunoreactive group. The complexing agent and the metal radionuclide can be complexed either before or after the complexing agent is attached to the immunoreactive group. As used herein the term "immunoreactive group" is meant to include any organic compound which is capable of covalently bonding to the complexing agent and which is found in a living organism or is useful in the diagnosis, treatment or genetic engineering of cellular material or living organisms, and which has a capacity for interaction with another component which may be found in biological fluids or associated with cells to be treated such as tumor cells.

Depending upon the intended use, the immunoreactive group can be selected from a wide variety of naturally occurring or synthetically prepared materials, including, but not limited to enzymes, amino acids, peptides, polypeptides, proteins, lipoproteins, glycoproteins, hormones, drugs (for example digoxin, phenytoin, phenobarbitol, thyrozine, triiodothyronine, gentamicin, carbamazepine, and theophylline), steroids, vitamins, polysaccharides, viruses, protozoa, fungi, parasites, rickettsia, molds, and components thereof, blood components, tissue and organ components, pharmaceuticals, haptens, lectins, toxins, nucleic acids (including oligonucleotides), antibodies, antigenic materials (including proteins and carbohydrates), avidin and derivatives thereof, biotin and derivatives thereof, and others known to one skilled in the art.

Preferred immunoreactive groups for use in the practice of this invention are those which have a receptor molecule specific to a ligand of interest. Thus, a specific binding reaction involving the reagent can be used for the targeting expected. Examples of such ligand-receptor complexes include, but are not limited to antibody-antigen, avidin-biotin, repressor (inducer)—promoter of operons and sugar-lectin complexes. Additionally, complementary nucleic acids, i.e., a hybridized product of complementary strands, are also considered specific binding materials as the term is used herein.

Useful immunoreactive groups include (1) any substance which, when presented to an immunocompetent host, will result in the production of a specific antibody capable of binding with that substance, or (2) the antibody so produced, which participates in an antigen-antibody reaction. Thus, the immunoreactive group can be an antigenic material, an antibody, or an anti-antibody. Both monoclonal and polyclonal antibodies are useful. The antibodies can be whole molecules or various fragments thereof, as long as they contain at least one reactive site for reaction with the reactive groups on the complexing agent or with linking groups as described herein.

In certain embodiments, the immunoreactive group can be an enzyme which has a reactive group for attachment to the complexing agent. Representative enzymes include, but are not limited to, aspartate aminotransaminase, alanine aminotransaminase, lactate dehydrogenase, creatine phosphokinase, gamma glutamyl transferase, alkaline acid phosphatase, prostatic acid phosphatase, horseradish peroxidase and various esterases.

If desired, the immunoreactive group can be modified or chemically altered to provide reactive groups for attaching to the complexing agent by techniques known to those skilled in the art. Such techniques include the use of linking moieties and chemical modification such as described in WO-A- 89/02931 and WO-A-89/2932, which are directed to modification of oligonucleotides, and U.S. Pat. No. 4,719, 182 the disclosures of which are hereby incorporated by reference in their entirety.

Two highly preferred uses of the targeting immunoreagents of this invention are for the diagnostic imaging of tumors and the radiological treatment of tumors. Preferred immunological groups therefore include antibodies to tumor-associated antigens. Specific examples include B72.3 antibodies (described in U.S. Pat. Nos. 4,522,918 and 4,612, 282) which recognize colorectal tumors, 9.2.27 anti-melanoma antibodies, D612 antibodies which recognize colorectal tumors, UJ13A antibodies which recognize small cell lung carcinomas, NRLU-10 antibodies which recognize small cell lung carcinomas and colorectal tumors (Pancarcinoma), 7E11C5 antibodies which recognize prostate tumors, CC49 antibodies which recognize colorectal tumors, TNT antibodies which recognize necrotic tissue, PR1A3 antibodies, which recognize colon carcinoma, ING- 1 antibodies, which are described in International Patent Publication WO-A-90/02569, B174 antibodies which recognize squamous cell carcinomas, B43 antibodies which are reactive with certain lymphomas and leukemias and others which may be of particular interest.

Such antibodies and other useful immunological groups described above are large, complex molecules having multiple sites for appendage of the complexing agent. Consequently, the immunoreactive group can have appended to it additional complexing agents via one of the protein reactive groups. Thus, the term immunoreactive group is intended to include immunological groups having complexing agent molecules bonded thereto through one or more protein reactive groups.

Additionally, an antibody or fragment thereof containing a carbohydrate region can be attached to the complexing agent through the carbohydrate region of the antibody, such as described in U.S. Pat. No. 4,937,183, the disclosure of which is hereby incorporated by reference in its entirety. Useful methods for attaching an antibody are also described in U.S. Pat. Nos. 4,671,958; 4,699,784; 4,741,900; and 4,867,973. The term "protein reactive group" as defined herein is intended to include such linkages.

Other techniques for performing the covalent binding of the immunoreactive group to the radioactive metal complexing agents are known in the art and include simply mixing the materials together.

The radioactive immunoreagent of this invention can contain any ratio of metal radionuclide ion to complexing agent. In preferred embodiments, the mole ratio of metal ion to complexing agent is from about 1:100 to about 1:1.

The ratio of chelate to immunoreactant can vary widely from about 0.5:1 to 10:1 or more. In some embodiments, the mole ratio of chelate to immunoreactive groups is from about 1:1 to about 6:1.

Figure 6:
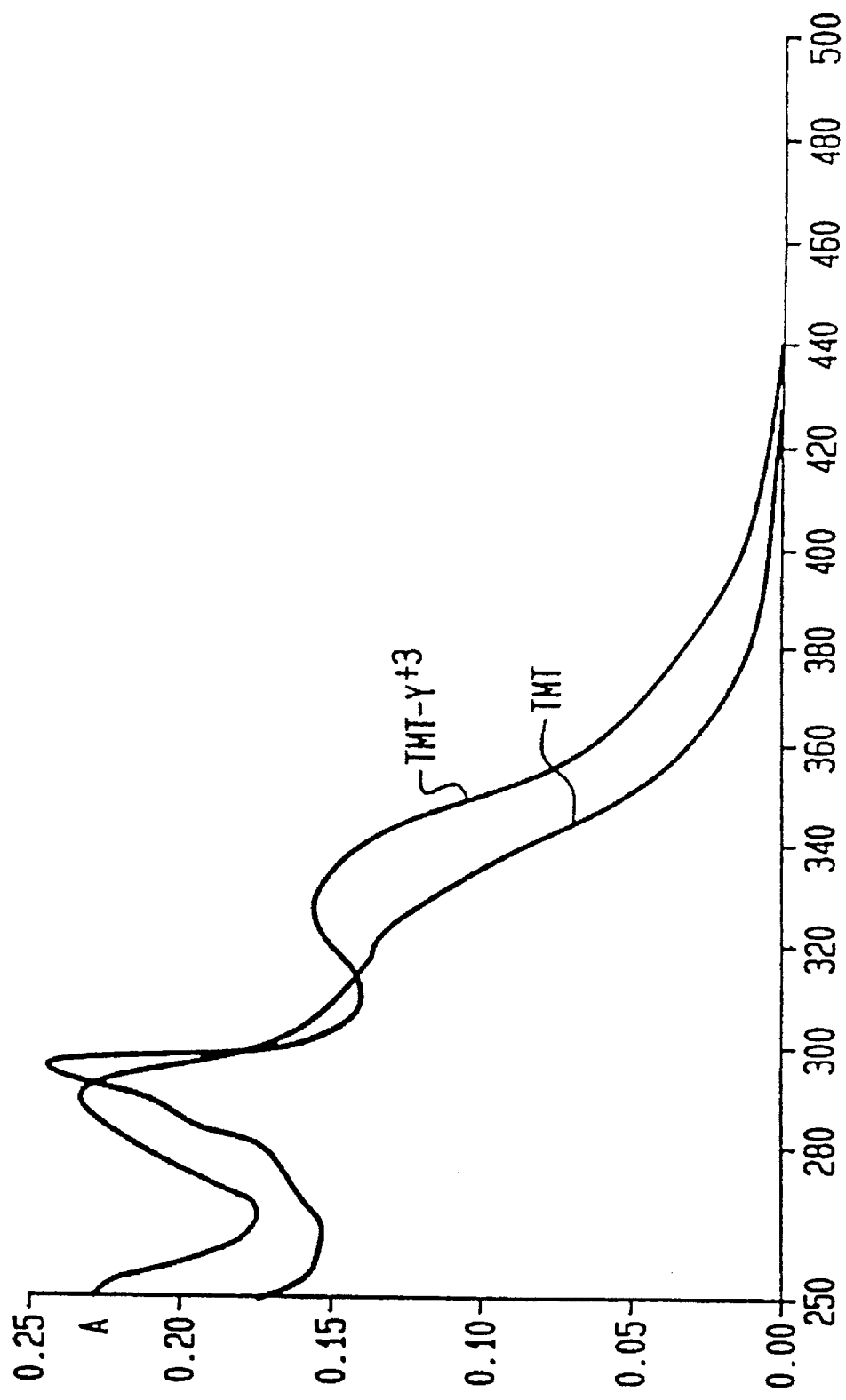
FIGS. 6 and 7 are spectra of TMT, TMT-Y⁺⁺⁺ and TMT-Pb⁺⁺.
Figure 7:
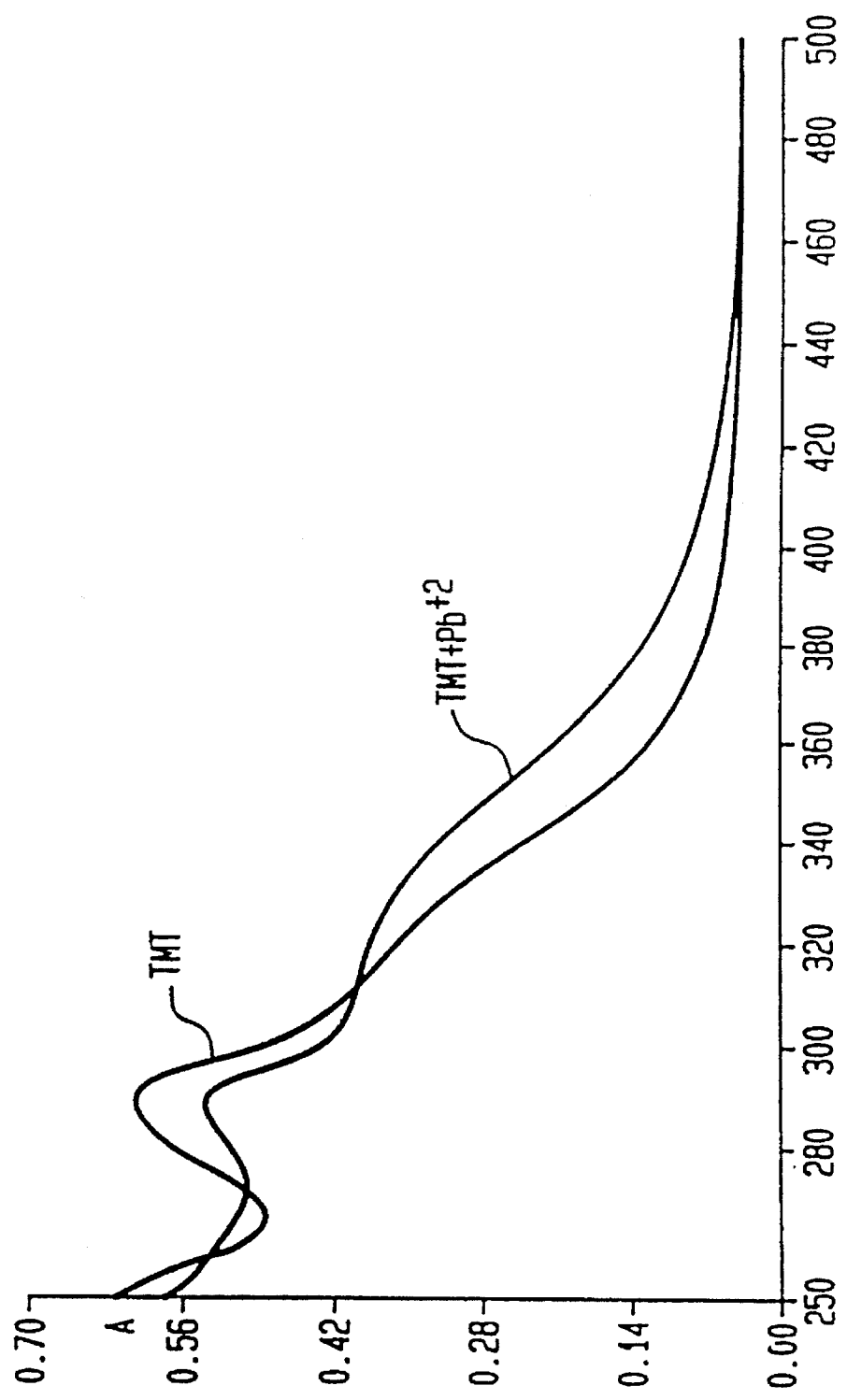

FIGS. 6 and 7 are spectra of complexing agents and metal complexes of this invention. Portions of the spectra do not overlap with those of the proteins to which the chelating agents are chemically bonded. Similar spectral shifts were obtained between chelating agents of this invention and other representative cations such as $Ga^{+3}$, $Bi^{+3}$, $In^{+3}$, $Sc^{+3}$ and $Cu^{+2}$. Thus, the immunoreagent of this invention can be readily spectrophotometrically analyzed.

The following examples further illustrate the invention:

Preparation 1 Preparation of 4'-(3-Amino-4-methoxyphenyl)-6,6'-[N,N-di(carboxymethyl)aminomethyl]-2,2'; 6',2"-terpyridine, Tetrasodium Salt (TMT)

Part A—Pyridinium Bromide 1

2-Acetyl-6-bromopyridine was synthesized by the method of J. E. Parks, B. E. Wagner, and R. E. Holm, *J. Organometal. Chem* 56, 53–66 (1973). 2-Acetyl-6-bromopyridine (20.0 g, 100 mmol) was treated with bromine (6.2 mL, 0.12 mol) at reflux in 200 mL of $CHCl_3$ for 45 min. The solution was cooled to room temperature then washed with dilute aqueous $NaHCO_3/Na_2S_2O_3$. The organic phase was dried over $Na_2SO_4$, filtered, and evaporated to give an oil. The oil was dissolved in 200 mL of THF and 30 mL of pyridine was added. The resulting solution was refluxed for 30 min. The mixture was cooled and filtered to give 26.1 g of off-white powder (73%): mp 256° C. dec (discolors at 245° C.). Anal. Calcd. for $C_{12}H_{10}Br_2N_2O$: C, 40.26; H, 2.82; N, 7.82. Found: C, 40.12; H, 2.85; N, 7.79. The NMR and IR spectra were consistent with the assigned structure and the product was homogeneous by TLC.

Part B—Chalcone 2

Potassium hydroxide (18.2 g, 325 mmol) was dissolved in 100 mL of $H_2O$, and 100 mL of methanol was added. 2-Acetyl-6-bromopyridine (65 g, 325 mmol) and (68 g, 650 retool) of p-anisaldehyde were dissolved together in 400 mL of methanol, and the solution was poured into the KOH solution. Precipitation of product began Within a few minutes, and the reaction was allowed to stand at room temperature overnight. The precipitate was collected, washed with isopropanol, and dried to yield 79 g (76%) of the product as a yellow solid, mp 100°–102° C. FDMS (m/e) 317M. An aliquot was purified by column chromatography on Woelm Silica gel, elution with 100% dichloromethane. Anal. Calcd for $C_{15}H_{12}BrNO_2$: C, 56.63; H, 3.80; N, 4.40. Found: C, 6.66;H, 3.87; N, 4.41. The NMR and IR spectra were consistent with the assigned structure and the product was homogeneous by TLC.

Part C—Dibromoterpyridine 3

Pyridinium bromide 1 (11.3 g, 31.6 mmol) and chalcone 2 (10.0 g, 31.4 mmol) were refluxed in 100 mL of AcOH with 10 g of $NH_4OAc$ for 16 hours. The solution was cooled and filtered, and the solid was washed with AcOH then EtOH to give 13.48 g of white crystals (86%): mp 203°–204.5° C. FDMS (m/e) 495 (M+). Anal. Calcd for $C_{22}H_{15}Br_2N_3O$: C, 53,1; H, 3.0; N, 8.5. Found: C, 52.9; H, 3.1; N, 8.4. The NMR and IR spectra were consistent with the assigned structure and the product was homogeneous by TLC.

Part D—Terpyridinediol 6

Dibromide 3 (7.46 g, 15.5 mmol) in 100 mL of dry THF was added dropwise to a solution of 28.1 mL of 1.6M n-BuLi in 20 mL of dry THF under $N_2$ over a 12 min period. The temperature was maintained below −75° C. during the addition with a dry ice/acetone bath. The resulting dark green solution was stirred for 10 minutes followed by addition of 7.5 mL of dry DMF over a 2 min period. After 10 min, 90 mL of a 10% HCl solution was added and the resulting solution was stirred for 45 min with continued cooling. The mixture was partitioned between $CHCl_3$ and $H_2O$ (both solvents pre-cooled to 4° C.) in a separatory funnel. The phases were shaken frequently and allowed to stand at ambient temperature for 15–30 minutes, until the color of the organic phase gradually changed from a greenish hue to golden yellow. The organic phase was washed with sat. NaCl then evaporated to leave a cream-colored residue. This material was triturated with $CH_3CN$ to yield the product as an off-white solid (3.53 g, 60%), mp 225°–227° C. FDMS (m/e) 395M. Anal. Calcd for $C_{24}H_{17}N_3O_3$: C, 72.90; H, 4.33; N 10.63. Found: C, 72.44; H, 4.31; N, 10.46.

The crude dialdehyde (3.53 g, 8.93 mmol) was refluxed with 1 g of $NaBH_4$ in a mixture of 70 mL of THF and 70 mL of abs. EtOH for 15 min under $N_2$. After concentration in vacuo, the residue was refluxed for 30 min in dilute $NaHCO_3$, cooled, filtered, washed with $H_2O$, then dried to give diol 6 as a white solid (3.35 g, 94.4%). mp 187°–189° C. FDMS (m/e) 400 $MH^+$, 399M. Anal. Calcd for $C_{24}H_{21}N_3O_3$: C, 72.17; H, 5.30; N, 10.52. Found: C, 71.71; H, 5.20; N, 10.37. The NMR and IR spectra were consistent with the assigned structure and the product was homogeneous by TLC.

Part E—Tetraester 7

Diol 6 (15.4 g, 38.5 mmol) was suspended in a mixture of 17 mL of Et3N in 175 mL of $CH_2Cl_2$ with stirring at 8° C. To this suspension, a solution of$(CH_3SO_2)20$ (16.8 g, 96.5 mmol) in 50 mL of $CH_2Cl_2$ was added dropwise over a 10 min period. The reaction mixture was shaken with water. The organic layer was dried over $Mg_2SO_4$, filtered, and concentrated nearly to dryness. Addition of EtOAc produced the bismesylate as white crystals which were collected and dried (17.2 g, 80.4%). A mixture of the bismesylate (0.50 g, 0.96 mmol), diisopropylethylamine (0.26 g, 2.0 mmol), and diethyliminodiacetate (0.38 g, 2.0 mmol) was stirred for 16 hours in 20 mL of dry DMF. The mixture was concentrated in vacuo and the residue was partitioned between $Et_2O$ and $H_2O$. The $Et_2O$ phase was washed two additional times with water then dried over $Na_2SO_4$ and evaporated to give the product as a pale yellow oil (0.58 g, 82%). Anal. calcd for $C_{40}H_{47}N_5O_9$: C, 64.76; H, 6.39; N, 9.44. Found: C, 64.35; H, 6.17; N, 9.39. The NMR and IR spectra were consistent with the assigned structure and the product was homogeneous by TLC.

Part F—Nitrotetraester 8

Terpyridine tetraester 7 (3.27 g, 4.41 mmol) was dissolved in 60 mL of conc. $H_2SO_4$ to give a red-orange solution. The mixture was cooled to 0° C. and a 1/10 (v/v) mixture of conc. $HNO_3$ in conc. $H_2SO_4$ was added such that 4.41 mmol of $HNO_3$ was delivered. The color of the solution turned pale yellow after addition was completed. The reaction mixture was stirred for 15 min at 0° C., then poured onto crushed ice. Dilute $K_2CO_3$ was added until pH 8 was reached. The aqueous solution was extracted three times with $CH_2Cl_2$. The organic layers were combined, dried over $Na_2SO_4$, and concentrated to give a yellow oil, which was chromatographed on silica gel (5% $MeOH/CH_2Cl_2$). The fractions containing product were combined and evaporated to give the product which was recrystallized three times from MeOH to yield an off-white solid (1.84 g, 53%): mp 76°–79° C. FDMS (m/e) 787 $MH^+$, 786M. Anal. calcd for $C_{40}H_{46}N_6O_{11}$: C, 61.06; H, 5.89; N, 10.68. Found: C, 60.69; H, 6.22; N, 11.04. The NMR and IR spectra were consistent with the assigned structure and the product was homogeneous by TLC.

Part G—Aminoterpyridine Tetraester 9

Nitrotetraester 8 (1.80 g, 2.29 mmol) was dissolved in a mixture of 90 mL of THF and 90 mL of abs. EtOH. Ammonium formate (2.89 g, 45.8 mmol) dissolved in 16 mL of $H_2O$ was added, followed by 4.8 g of 10% Pd/C (4.6 mmol). After stirring at room temperature for 2 h, the reaction was filtered through a diatomaceous earth filter pad. The filter pad was washed well with THF, abs. EtOH, and $CH_2Cl_2$. The filtrate was concentrated, and the residue was partitioned between $CH_2Cl_2$ and aqueous NaCl. The organic phase was concentrated then purified on $SiO_2$ with 10% $MeOH/CHCl_3$ to give the product as a straw-colored oil (0.80 g, 46%). FDMS (m/e) 757 $MH^+$, 756M. Anal. calcd for $C_{40}H_{48}N_6O_9 \cdot \frac{1}{2}H_2O$: C, 62.73; H, 6.45; N, 10.97. Found: C, 62.98; H, 6.47; N, 10.67. The NMR and IR spectra were consistent with the assigned structure and the product was homogeneous by TLC.

Part H—Aminotetraacid 10 (TMT)

Amine tetraester 9 (0.75 g, 0.99 mmol) was stirred with 4 equiv of NaOH in a mixture of 50 mL of MeOH and 2 mL of $H_2O$ for 16 hours at room temperature. The mixture was concentrated to give the product as a solid dihydrate (0.72 g, 94%): FABMS m/e 640 (M+ for tetracarboxylate). Anal. calcd. for $C_{32}H_{28}N_6Na_4O_9 \cdot 2H_2O$: C, 50.01; H, 4.20; N, 10.93. Found: C, 49.82; H, 4.12; N, 10.74. The NMR and IR spectra were consistent with the assigned structure and the product was homogeneous by TLC.

Preparation 2 Preparation of 4'-(3-amino-4-methoxyphenyl)-6,6"-bis(N'N'-dicarboxymethyl-N-methylhydrazino)-2,2';6',2"-terpyridine, tetrasodium salt (THT)

Part A—6,6"-Bis(N-methylhydrazino)-4'-(4-methoxy-phenyl)-2,2';6',2"-terpyridine 6,6"-Dibromo-4'-(4-methoxyphenyl)- 2,2':6',2"-terpyridine (1.0 g, 2 mmol) was refluxed in 20 mL of methylhydrazine for 16 hours under nitrogen. The solution was cooled, and the resulting precipitate filtered, and dried to a constant weight to give 0.68 g of cream-colored solid, mp 218°–220° C. FDMS (m/e) 428 $MH^+$, $427M^+$. Anal. calcd for $C_{24}H_{25}N_7 \cdot 0.25\ H_2O$: C, 66.72; H, 5.96; N, 22.70. Found: C, 66.85; H, 5.85; N, 23.0. The NMR and IR spectra were consistent with the assigned structure.

Part B—6,6"-Bis(N',N'-di(ethoxycarbonylmethyl)-N-methylhydrazino)- 4'-(4-methoxyphenyl)- 2,2':6',2"-terpyridine The bis(methylhydrazine)terpyridine of Part A (3.50 g, 82 mmol), ethyl bromoacetate (13.2 mL, 820 mmol), 2,6-lutidine (9.6 mL, 820 mmol), and sodium iodide (0.35 g, 2 mmol) were added to 350 mL of acetonitrile, and the solution was refluxed under $N_2$ for 48 hours, when an additional 4.1 mL (370 mmol) of ethyl bromoacetate and 4.8 mL (410 mmol) of 2,6-lutidine were added. The reaction solution was refluxed for an additional 48 hours, and cooled. A copious amount of white salt resulting from excess bromoacetate and lutidine was filtered and discarded. The filtrate was concentrated, and the concentrated material was dissolved in dichloromethane, and extracted two times with dilute aqueous sodium chloride. The organic phase was concentrated under high vacuum until free of odors of bromoacetate and lutidine. The crude oil was purified on a Woelm silica gel column (36×2 in.). The column was eluted initially with 100% dichloromethane followed by 50/1 dichloromethane/acetone, with gradual increase of the concentration of acetone to 25/1 dichloromethane/acetone. Concentration of purified fractions gave 2.91 g (46%) of light straw-colored oil. A fraction of the purified oil, upon standing at room temperature, crystallized, and after trituration with methanol gave a white solid, mp 100°–103° C. Anal. calcd for $C_{40}H_{49}N_7O_9$: C, 62.24; H, 6.40; N, 12.70. Found: C, 62.31; H, 6.32; N, 12.69. The NMR and IR spectra were consistent with the assigned structure, and the product was homogeneous by TLC.

Part C—6,6"-Bis (N',N'-di(ethoxycarbonylmethyl)-N-methylhydrazino)- 4'-(4-methoxy-3-nitrophenyl)- 2,2':6',2"-terpyridine The terpyridine tetraester of Part B (0.659 g, 0.84 mmol) was dissolved in 5 mL of conc $H_2SO_4$ to give a red-orange solution. The mixture was cooled to 0° C., and a mixture of conc $HNO_3$ in conc $H_2SO_4$ was added such that 0.84 mmol of $HNO_3$ was delivered. The color of the solution turned pale yellow after addition was completed. The reaction mixture was stirred for 15 minutes at 0° C. then poured onto crushed ice Dilute $K_2CO_3$ was added until pH 8 was reached. The aqueous solution was extracted three times with $CH_2Cl_2$. The organic layers were combined and dried over $Na_2SO_4$, and concentrated to give a yellow oil, which was chromatographed on silica gel (20/1 methylene chloride/acetone). The fractions containing product were combined and evaporated to give the product, a pale yellow glass. Yield 0.15 g (22%). Anal. calcd for $C_{40}H_{48}N_8O_{11}$: C, 58.82; H, 5.92; N, 13.72. Found: C, 58.76; H, 5.61; N, 13.84. FDMS (m/e) 816M. The NMR and IR spectra were consistent with the assigned structure, and the product was homogeneous by TLC.

Part D—4'-(3-Amino-4-methoxyphenyl)-6,6"-bis(N',N'-di(ethoxycarbonylmethyl)-N-methylhydrazino)- 2,2': 6',2"-terpyridine The nitrotetraester of Part C (0.72 g, 0.88 mmol) was dissolved in a mixture of 30 mL of THF and 30 mL of ethanol. Ammonium formate (1.08 g, 17.1 mmol) dissolved in 6 mL $H_2O$ was added, followed by 1.8 g of 10% Pd/C (1.7 mmol). After stirring at room temperature overnight, the reaction was filtered through a diatomaceous earth filter pad. The filter pad was washed well with THF, absolute EtOH, and $CH_2Cl_2$. The filtrate was concentrated, and the residue was dissolved in chloroform, and the chloroform solution was washed two times with water. The organic phase was concentrated to an oil. Addition of methanol to the oil resulted in crystallization of the oil. The material was slurried in 20 mL of methanol, and filtered, and air dried to yield 0.64 g of cream colored solid (92.7%). Anal. calcd for $C_{40}H_{50}N_8O_9$: C, 61.06, H, 6.40; N, 14.24. Found: C, 60.74; H, 6.39; N, 14.01. The NMR and IR spectra were consistent with the assigned structure and the product was homogeneous by TLC.

Part E—4'-(3-Amino-4-methoxyphenyl)-6-6"-bis(N',N'-dicarboxymethyl-N-methylhydrazino)-2,2': 6',2"-terpyridine, tetrasodium salt (THT)

The amine tetra ester of Part D (0.60 g, 0.76 mmol) was stirred with 4 equivalents of NaOH in a mixture of 25 mL of MeOH and 1 mL of $H_2O$ for about 16 hrs at room temperature. The mixture was concentrated to give a quantitative yield of solid tetracarboxylate. Anal. calcd for $C_{32}H_{30}N_8Na_4O_9.2H_2O$: C, 48.12; H, 4.29; N, 14.03. Found: C, 48.01; H, 3.97; N, 12.77.

Preparation 3 Preparation of
6,6"-Bis(N',N'-di-carboxymethyl-N-methylhydrazino)-
4'-(3-isocyanato-4-methoxyphenyl)-2,2':6',2"-terpyridine,
Sodium Salt The THT amine tetrasodium salt of Preparation 2, Part E (0.39 g, 0.51 mmol) was dissolved in 80 mL of methanol. At room temperature, 0.58 g (0.50 mmol) of thiophosgene in 1.0 mL tetrahydrofuran was added, followed by addition of 0.51 g (0.50 mmol) of triethylamine in 1.0 mL of tetrahydrofuran. The reaction was then concentrated to a residue, which was slurried in dichloromethane, and filtered to yield 0.26 g (65%) of yellow solid. The infrared spectrum was consistent with the assigned structure. The product 5 was believed to be the monocarboxylic acid trisodium salt.

Preparation 4 Preparation of
5-Amino-2,9-Bis[N,N-di-(carboxymethyl)
aminomethyl]-1,10-phenanthroline, Tetrasodium
Salt Part A—2,9-Dimethyl-5-nitro-1,10-phenanthroline Neocuproine hydrochloride, hemihydrate (25.0 g, 99 mmol) was dissolved in 100 mL of concentrated nitric acid. 200 mL of concentrated sulfuric acid was added, and the reaction was heated at reflux for 2.5 hours, and then allowed to stand at room temperature for 8 days. The reaction mixture was then gradually added to a mixture of about 3 Kg of ice and 351 g (8.8 mole) of $LiOH.H_2O$, while stirring with a glass rod. During the neutralization procedure, ice was added as necessary so that unmelted ice was always present during the neutralization, and the neutralization reaction was also simultaneously cooled by an acetone/ice bath. After the addition was completed, the pH of the reaction mixture was 12. The aqueous mixture was extracted two times with methylene chloride, first with 1000 mL, and then with 400 mL. The methylene chloride fractions were combined, and extracted once with 500 mL of distilled $H_2O$. The methylene chloride phase was concentrated to a residue, and triturated with 500 mL of acetonitrile. The solid was filtered, washed with acetonitrile, and dried under vacuum to give 10.3 g of cream yellow solid, which was dissolved in 100 mL of refluxing acetonitrile, allowed to crystallize at room temperature, and was filtered to give 8.5 g (34%) of cream-yellow crystals, mp 184°–186° C. FDMS (m/e) 253M. Anal. calcd for $C_{14}H_{11}N_3O_2.0.25 H_2O$: C, 65.23; H, 4.50; N, 16.30. Found: C, 65.57; H, 4.45; N, 16.27. The NMR and IR spectra were consistent with the assigned structure and the product was homogeneous by TLC.

Part
B—2,9-Di(bromomethyl)-5-nitro-1,10-phenanthroline 2,9-Dimethyl-5-nitro-1,10-phenanthroline (1.0 g, 4 mmol) and N-Bromosuccinimide (1.42 g, 8 mmol) were mixed together into a homogeneous mixture in a beaker, and added all at once to 20 mL of refluxing (181° C.) o-dichlorobenzene. The heating was continued at the reflux temperature for 2 minutes, and then the reaction was allowed to cool to room temperature. The reaction mixture was purified on a column (18×2 in.) of Woelm silica gel, by elution with 100% dichloromethane, to give 0.47 g (29%) of purified material, a yellow oil. Rf on TLC, 0.5 (40/1 $CH_2Cl_2$/acetone). Trituration of an aliquot of the purified product gave a gray-white solid, which decomposed at 146° C. Anal. calcd for $C_{14}H_9Br_2N_3O_2.0.5 H_2O$: C, 40.02; H, 2.39; N, 10.00. Found: C, 40.36; H, 2.67; N, 9.77. FDMS (m/e) 409M. The NMR and IR spectra were consistent with the 0 assigned structure.

Part C—2,9-Bis
[N,N-di(ethoxycarbonylmethyl)aminomethyl]
-5-nitro-1,10-phenanthroline 2,9-Di(bromomethyl)-5-nitro-1,10-phenanthroline (2.28 g, 5.5 mmol) and 2.08 g (11 mmol) of 1,8-bis(dimethylamino) naphthalene were dissolved together in 25 mL of 1-methyl-2-pyrrolidinone, and 2.08 g (11 mmol) of diethyl iminodiacetate was added. The reaction was sealed with a ground glass stopper, and after approximately 10 minutes of stirring at room temperature, white precipitate began forming. The reaction was then placed in the refrigerator (at 4° C.) and stored for about 20 hours. The reaction mixture was partitioned between 400 mL of diethyl ether and 400 mL of distilled $H_2O$ and the ether fraction was extracted a total of 5 times with 400 mL portions of distilled $H_2O$. The ether phase was concentrated and dissolved in 400 mL of methylene chloride. The methylene chloride phase was extracted once with distilled $H_2O$, dried with a mixture of Celite diatomaceous earth and sodium sulfate, and then filtered, and concentrated to a dark oil. A column of Woelm silica gel was prepared in 10/1 methylene chloride/methanol (20 inches in height by 2 inches in diameter), and the crude oil was applied to the column in minimal methylene chloride. About 50 mL of methylene chloride was applied to the column, and then the column was eluted with 10/1 $CH_2Cl_2$/methanol. Fractions (100 mL each) were collected, and the fractions of pure product by TLC (10/1 methylene chloride/methanol, Rf 0.4) were combined and concentrated to yield 1.17 g (34%) of product, an oil of reddish-amber due. FDMS (m/e) 628 $MH^+$. Anal calcd for $C_{30}H_{37}N_5O_{10}.2H_2O$: C, 54.29; H, 6.23; N, 10.55. Found: C, 54.71; H, 5.58; N, 10.53. The NMR and IR spectra were consistent with the assigned structure.

Part
D—5-Amino-2,9-bis[N,N-di(ethoxycarbonylmethyl)
aminomethyl] -1,10-phenanthroline 2,9-Bis[N,N-di(ethoxycarbonylmethyl)aminomethyl] -5-nitro-1,10-phenanthroline (3.37 g, 5.4 mmol) was dissolved in a solution of 100 mL tetrahydrofuran and 200 mL absolute ethanol. A solution of 6.8 g (108 mmol) of ammonium formate in 22 mL of distilled $H_2O$ was added, followed by 5.72 g of Palladium on carbon (10%) (50% wet with water for safety). The reaction was stoppered with a gas bubbler, stirred at room temperature for 30 minutes, and then filtered through a diatomaceous earth filter pad. The solvents were then removed by a rotary evaporator. The residue was dissolved in 300 mL of dichloromethane, which was then extracted with 300 mL of distilled water. The organic phase was then extracted with 300 mL of saturated sodium chloride, then dried with a mixture of Celite diatomaceous earth and sodium sulfate, filtered, and concentrated under high vacuum to a dark amber oil which weighed 2.90 g. The oil was treated with 9.0 mL of propionitrile, which resulted in the crystallization of a yellow solid. The solid was filtered, and washed with 13 mL of propionitrile, and finally washed with 15 mL of hexanes, and air dried to a constant weight of 1.04 g (32%) mp 137°–139° C. FDMS (m/e) 598 $MH^+$, 597M. Anal. calcd for $C_{30}H_{39}N_5O_9.H_2O$: C, 58.52; H, 6.71; N, 1.38. Found: C, 58.28; H, 6.55; N, 11.53. The NMR and IR spectra were consistent with the assigned structure.

Part E—5-Amino-2,9-bis[N,N-di(carboxymethyl) aminomethyl] -1,10-phenanthroline, Tetrasodium Salt 5-Amino-2,9-bis[N,N-di(ethoxycarbonylmethyl)aminomethyl] -1,10-phenanthroline (0.90 g, 1.5 mmol) was dissolved in 200 mL of methanol. Sodium hydroxide (0.25 g, 6.25 mmol) dissolved in 10.0 mL of distilled $H_2O$ was added. The reaction was stoppered and stirred by magnetic stirring for 24 hours at room temperature. The solvent was removed by rotary evaporation, and the solid residue was triturated with methylene chloride and filtered to yield 0.81 g (94%). The tetrasodium salt was hygroscopic, and a significant amount remained adhered to the glass wall of the filtration funnel. Anal. calcd for $C_{22}H_{19}Na_4N_5O_8 \cdot 3H_2O$: C, 42.11; H, 4.02; N, 11.16. Found: C, 42.01; H, 3.71; N, 11.03. The IR spectrum and FAB mass spectrum were consistent with the assigned structure.

Preparation 5 Preparation of 2,9-Bis[N,N-di(carboxymethyl)aminomethyl]-5-isothiocyanato- 1,10-phenanthroline, Sodium Salt 5-Amino-2,9-bis[N,N-di(carboxymethyl)-aminomethyl] -1,10-phenanthroline, tetrasodium salt (0.16 g, 0.28 mmol) was dissolved in a solvent mixture of 20 mL methanol/4 mL distilled $H_2O$. Thiophosgene (0.28 mmol, i.e., 1.0 mL of a solution of 0.32 g thiophosgene in 10.0 mL THF) was added, followed immediately by addition of 0.28 mmol of triethylamine (1.0 mL of a solution of 0.28 g of triethylamine in 10.0 mL THF). The reaction was carried out at room temperature, and was then immediately concentrated to a residue, 0.16 g (94%) of yellow solid. The IR spectrum was consistent with the assigned structure. The product was believed to be the monocarboxylic acid trisodium salt.

Preparation 6 Preparation of 6,6"-[N,N-di(carboxymethyl)aminomethyl]-4'-(3-isothiocyanato-4-methoxyphenyl)-2,2'-6',2"-terpyridine, Tetrasodium Salt The amino sodium tetracarboxylate of Preparation 1 (0.31 g, 0.42 mmol) was dissolved in 30 mL of methanol, 1.00 mL of THF containing 0.42 mmol of thiophosgene was added and then 1.00 mL of THF containing 0.42 mmol of triethylamine was also added. The reaction solution was immediately concentrated to a residue triturated with triethylamine, the solid collected by filtration and washed with dichloromethane to give 0.30 g of product. The IR spectrum was consistent with the assigned structure.

Preparation 7. Trisodium 15-amino-3,5,6,8,9,11-hexahydro-4,7,10-tris (carboxymethyl)-2,17:12,14-dietheno-1,4,7,10,13 -pentaazabenzocyclopentadecine

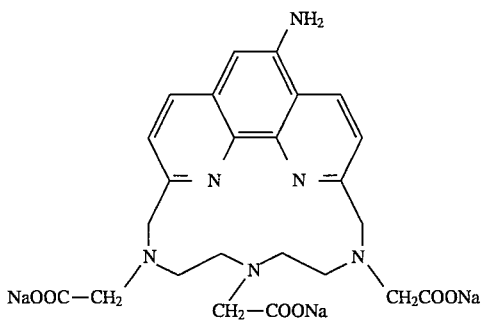

Part A. 3,5,6,8,9,11-Hexahydro-15-nitro-4,7,10-tris (p-toluenesulfonamido)- 2,17:12,14-dietheno-1,4,7,10,13-pentaazabenzocyclopentadecine

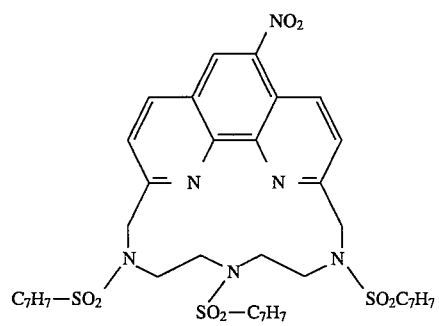

100 mL of N-methylpyrrolidin-2-one containing 2% by weight of 2,9-bisbromomethyl-5-nitro-1,10-phenanthroline prepared in Preparation 4, Part B is added via a syringe pump over 2 hours into 20 mL of magnetically stirred N-methylpyrrolidin- 2-one which is held under argon at 20° C. Simultaneously, a 2% solution in N-methylpyrrolidin-2-one of one equivalent of the disodium salt of diethylenetriamine N,N',N"-tri-p-toluenesulfonamide is added. The reaction is stirred for 6 additional hours after the addition at 20° C. 200 mL of the solvent is then distilled under high vacuum, the residual solution is cooled and added to 100 ml of ice water. The resulting precipitate is isolated by filtration, washed with cold water, and triturated with acetonitrile to provide the crude tri-p-toluenesulfonamide derivative.

Part B. 3,4,5,6,7,8,9,10,11-Nonahydro-15-nitro-2,17:12,14-dietheno-1,4,7,10,13-pentaazabenzocyclopentadecine

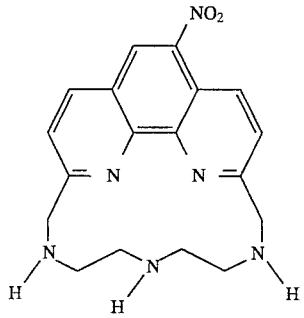

One part of crude macrocycle prepared in Part A is dissolved in 10 parts of concentrated sulfuric acid (96%), and the reaction mixture is stirred and heated to 110° C. under argon. After 24 hours, the solution is cooled with vigorous stirring in an ice water bath and is treated with 10% sodium hydroxide solution until the pH reaches 10. The aqueous phase is extracted five times with equal volumes of chloroform, the extracts are combined and are dried over anhydrous sodium sulfate. The salts are then removed by filtration, and the filtrate is evaporated under argon. The crude triamine can be purified by crystallization from ethanol/water.

Part C. 3,5,6,8,9,11-Hexahydro-15-nitro-4,7,10-tris(ethoxycarbonylmethyl)-2,17:12,14-dietheno-1,4,7,10,13-pentaazabenzocyclopentadecine

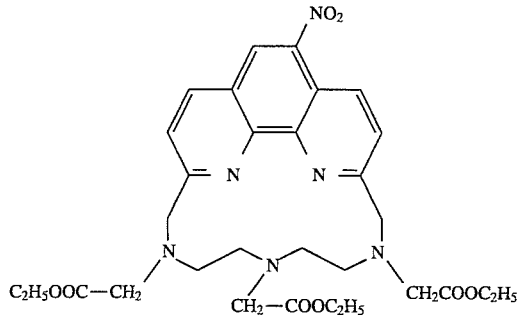

A mixture of one part of the triamino macrocycle prepared in Part B with 10 parts of sodium carbonate and 3 parts of ethyl bromoacetate as a 3 percent by weight solution in anhydrous acetonitrile is stirred under argon for 24 h at 60° C. The reaction mixture is then cooled to room temperature, filtered, the solvent is evaporated. The residue can be further purified by trituration in cold ether.

Part D. 15-Amino-3,5,6,8,9,11-hexahydro-4,7,10-tris(ethoxycarbonylmethyl)-2,17:12,14-dietheno-1,4,7,10,13-pentaazabenzocyclopentadecine

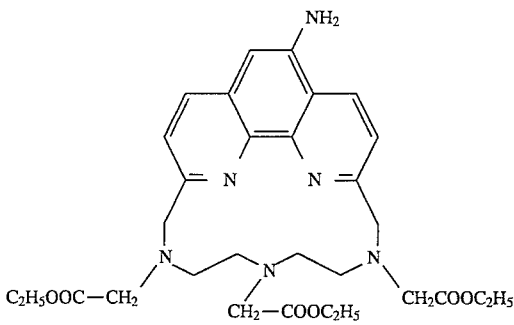

One part by weight of the nitrotriester of Part C can be dissolved in 100 parts by weight of a 50/50 mixture of tetrahydrofuran (THF) and ethanol. Two equivalents of ammonium formate in six times the weight of water is added followed by 2 equivalents of 10% Pd/C. The reaction mixture is stirred at room temperature overnight under argon, the reaction mixture is filtered under argon, and the filtered catalyst is washed well with THE, ethanol, and then dichloromethane under argon. The combined filtrate and washings are concentrated, the residue is dissolved in chloroform, and the choroform solution is washed twice with water. The organic phase is concentrated to an oil, and crystallization is promoted by the addition of methanol. The product is triturated in methanol, filtered, and then dried in air.

Part E. The amine triester of Part D is stirred at room temperature with three equivalents of sodium hydroxide in 5% aqueous methanol for 24 h. The solvent is removed under vaccuum and the product (A) is triturated with a little cold methanol. The product A can be isolated by filtration.

Preparation 8. Trisodium 15-isothiocyanato-4,7,10-tris(carboxymethyl)-2,17:12,14-dietheno-1,4,7,10,13-pentaazabenzocyclopentadecine

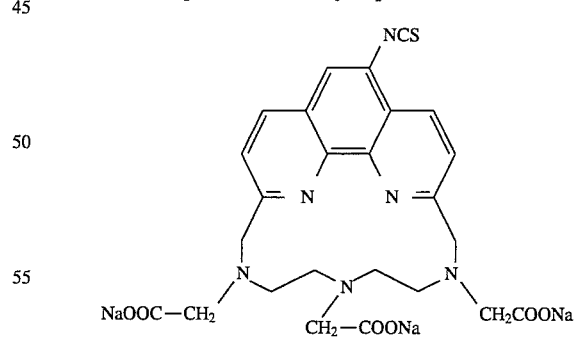

One part by weight of the amine trisodium salt from Preparation 7, Part E, is stirred in 200 parts of methanol at room temperature. This is treated at ambient temperature with one equivalent of thiophosgene dissolved in two parts by weight of tetrahydrofuran followed by one equivalent of triethylamine dissolved in two parts by weight of tetrahydrofuran. After one hour, the reaction mixture is concentrated to a residue, slurried in dichloromethane, and the product is isolated by filtration.

Preparation 9. Trisodium 2-Methyl-3-thio-4-{15-[3,5,6,8,9,11-hexahydro-4,7,10-tris(carboxymethyl)-2,17:12,14-dietheno-1,4,7,10,13-pentaazabenzocyclopentadecinyl]}-semicarbazide

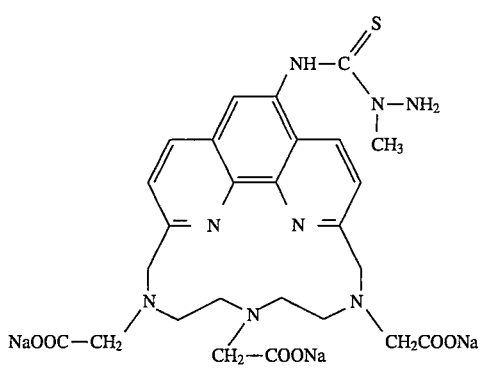

To a freshly prepared and stirred mixture of one part by weight of the trisodium salt of 15-isothiocyanato-4,7,10-tris(carboxymethyl)-2,17:12,14-dietheno-1,4,7,10,13-benzopentaazacyclopentadecine prepared in Preparation 8 and 200 parts by weight of methanol under argon at room temperature is rapidly added a solution of one equivalent of methylhydrazine dissolved in 10 parts of methanol. After one hour at room temperature, the solvent is removed by evaporation at reduced pressure, the residue is triturated with 10 parts of anhydrous oxygen-free ether, and the solid is isolated by filtration.

Preparation 10. Tetrasodium 2-Methyl-3-thio-4-{5-([6,6"-di-bis(carboxymethyl) aminomethyl]-2:2',6':2"-terpyridin4'-yl)-2-methoxyphenyl]}-semicarbazide

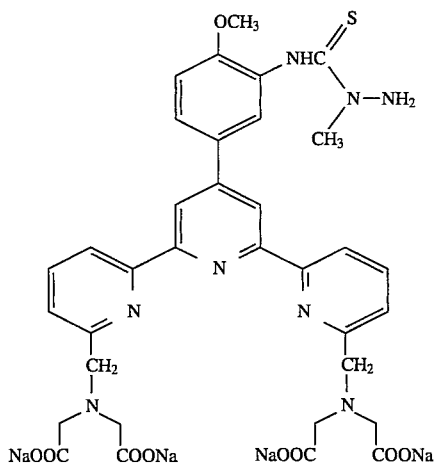

To a freshly prepared and stirred mixture of one part by weight of the tetrasodium salt of the TMT-isothiocyanate prepared in Preparation 6 and 200 parts by weight of methanol under argon at room temperature is rapidly added a solution of one equivalent of methylhydrazine dissolved in 10 parts of methanol. After one hour at room temperature, the solvent is removed by evaporation at reduced pressure, the residue is triturated with 10 parts of anhydrous oxygen-free ether, and the solid is isolated by filtration.

Preparation 11. Tetrasodium 2-methyl-3-thio-4-{5-([6,6"-bis(N',N'-dicarboxymethyl-N-methylhydrazino)-2:2',6:2"-terpyridine-4'-yl]-2-methoxyphenyl)}semicarbazide

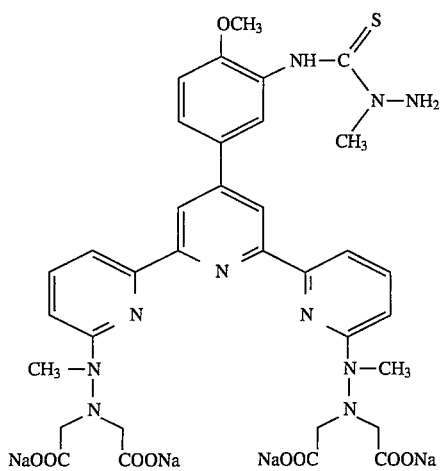

To a freshly prepared and stirred mixture of one part by weight of the tetrasodium salt of the THT-isothiocyanate prepared in Preparation 3 and 200 parts by weight of methanol under argon at room temperature is rapidly added a solution of one equivalent of methylhydrazine dissolved in 10 parts of methanol. After one hour at room temperature, the solvent is removed by evaporation at reduced pressure, the residue is triturated with 10 parts of anhydrous oxygen-free ether, and the solid is isolated by filtration.

Preparation 12. Tetrasodium 2-Methyl-3-thio-4-[2,9-di-bis(carboxymethyl)aminomethyl-1,10-phenanthrolin-5-yl]semicarbazide

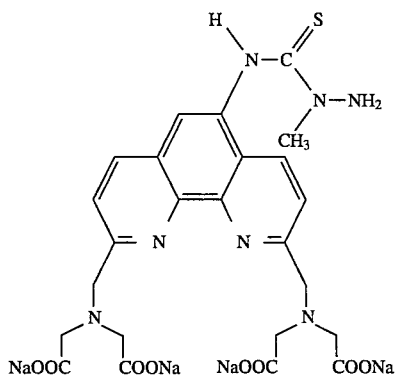

To a freshly prepared and stirred mixture of one part by weight of the tetrasodium salt of the PheMT-isothiocyanate prepared in Preparation 5 and 200 parts by weight of methanol under argon at room temperature is rapidly added a solution of one equivalent of methylhydrazine dissolved in 10 parts of methanol. After one hour at room temperature, the solvent is removed by evaporation at reduced pressure, the residue is triturated with 10 parts of anhydrous oxygen-free ether, and the solid is isolated by filtration.

Preparation of Conjugates of an Antibody with
TMT and with THT

Part A

Procedure to Attach Chelates to Antibodies

TMT or THT was attached to antibodies by oxidation of the carbohydrate groups on the antibodies with $NaIO_4$ to produce aldehyde groups on the antibodies. A solution (110 mL) of 0.1M $NaIO_4$ in purified water was added to one mL of a 4 mg/mL solution of B72.3* antibody in PBS (10 mM sodium phosphate, 0.15M NaCl), pH 6.0. The pH of the resulting solution was readjusted to 6.0 and incubated for 1 hour at room temperature in the dark. After this incubation, excess periodate was removed by passing the antibody solution through a Sephadex G50 column that had been equilibrated with PBS, pH 6.0. One mL fractions were collected and the two fractions giving the highest absorbance at 280 nm were pooled.

* B72.3 is a well known antibody to colorectal tumor-associated antigens which was first disclosed by the National Institute of Health (NIH).

A 0.33M. solution of each chelating agent (TMT or THT) was prepared by dissolving the solid chelating agent in PBS, pH 6.0. This raised the pH of the solution to over pH 9.0 so the pH was adjusted to about 6.8 with 6 M HCl. Two hundred µL of each chelator solution was added to separate 2 mL portions of the antibody solution and the pH of each resulting solution was adjusted to pH 6.0. These mixtures were incubated for 5 h at room temperature in the dark. Then $NaCNBH_3$ (Aldrich 29,694-5; 5M in about 1M NaOH) was added to each solution to a final concentration of 10 mM and the pH was adjusted to 6.0 to reduce the Schiff base formed by the aldehyde. The mixtures were incubated overnight at room temperature. The solutions were then centrifuged (Eppendorf Model 5412) to remove undissolved chelate that precipitated overnight and were concentrated to 1 mL in a Centricoh 30 (Amicon) microconcentrator. These solutions were passed through Sephadex G50 columns to remove excess chelator and $NaCNBH_3$. One mL fractions were collected and the two fractions of each chelator solution containing the highest absorbance at 280 nm were pooled. The pooled fractions were dialyzed against 0.01M sodium acetate, 0.15M NaCl, pH 6.0 with two changes of buffer. If further precipitates were formed during analysis, they were removed by centrifugation.

Typically, the conjugates produced by this procedure had a ratio of TMT or THT to antibody of about 1.7.

Part B—Analysis of Ratio of Chelator to Antibody

The concentrations of antibody in the conjugate solutions were determined using the BioRad protein assay using bovine immunoglobulin as the protein standard. The concentration of THT was determined spectrophotometrically using the measured extinction coefficient at 350 nm. For TMT-B72.3 conjugate a portion (about 0.5 mg) of the conjugate was put into 1 mL of 0.01M sodium acetate, 0.15M NaCl buffer, pH 6.0 and an excess of $Eu^{+3}$ was added. The absorbance of this solution at 330 nm was used to determine the amount of chelate in these solutions.

Part C—In Vitro Functional Test
(Immunocompetency Assay) of Antibody-Chelate
Conjugates The wells of Linbro EIA II Plus microtiter plates were coated with antigen by adding 100 µL/well of a solution of 4 µg/mL of bovine submaxillary mucin (Sigma M4503), an antigen to the B72.3 antibody, in PBS and incubated for 1 h at room temperature. After washing the plate three times with PBS, pH 6.8, the wells were blocked by adding 200 µL/well of a 1% BSA (bovine serum albumin, Sigma A-7906)-PBS, pH 6.8 solution and incubated for 1 h at room temperature. The plates were again washed three times with PBS, pH 6.8. Samples of the conjugates were prepared at a concentration of $1\times10^{-7}$M in PBS, pH 6.8 containing 1% horse serum (Sigma. S-7390), and dilutions in this same buffer were made from these solutions. One hundred mL of each sample dilution were added to wells, in duplicate. After a 1 h room temperature incubation, the plates were washed three times with PBS, pH 6.8 and then scored by the addition of 100 µl per well of a 1:1000 dilution of a rabbit anti-mouse F (ab')$_2$-HRP conjugate (Jackson Labs, 315-035-047) in PBS, pH 6.8, containing 1% horse serum. After a 1 h room temperature incubation, the wells were washed three times with PBS, pH 6.8. Color developed upon the addition of 100 µL per well of ABTS-HRP substrate (Kirkegaard and Perry Labs, Product #506502 and 506402). The reaction was stopped by the addition of an equal volume of 4N $H_2SO_4$. The color was read using a 414 nm filter in a Titertek Multiscan instrument after 15 min.

Figure 2:
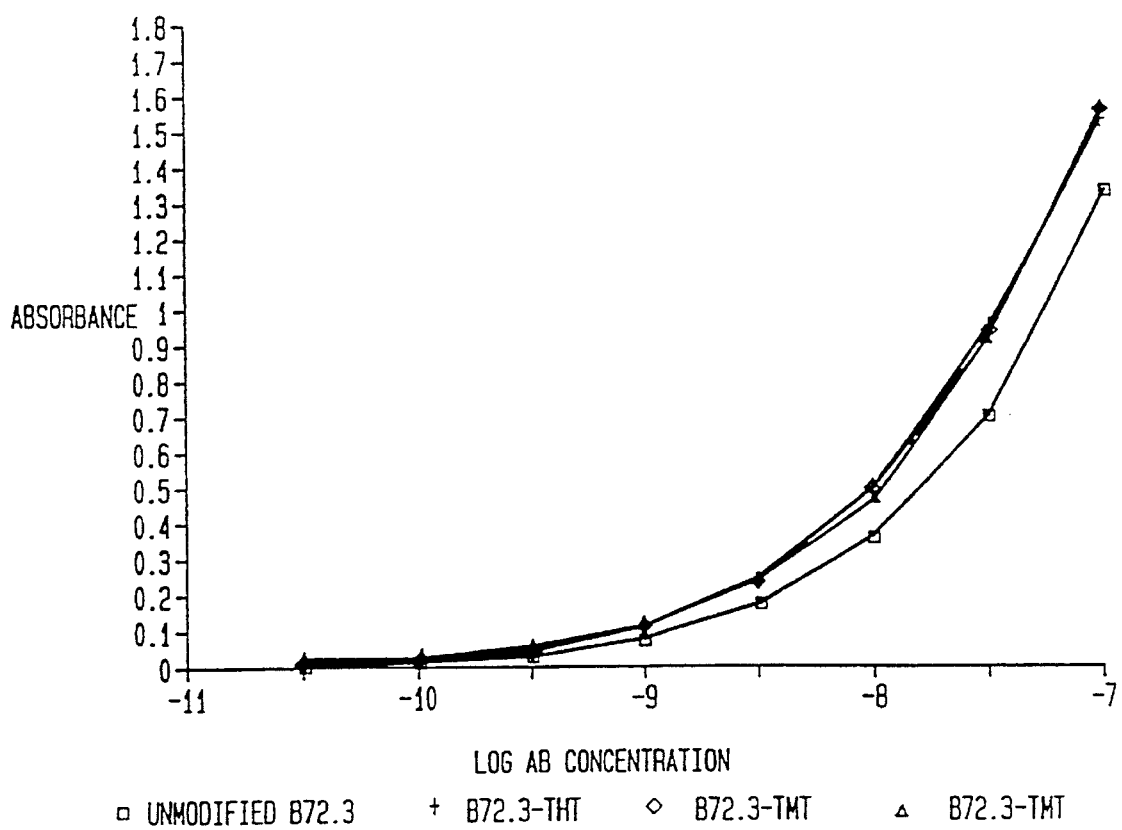
FIG. 2 depicts immunocompetency assays of a B72.3-THT conjugate, two preparations of B72.3-TMT conjugates and unmodified B72.3.

When tested by this procedure, the immunoconjugates of B72.3 with TMT or THT were found to have immunoreactivity comparable to native B72.3. The data are presented in FIGS. 1 and 2. FIG. 1 also contains the curve for a scandium complex of the B72.3—THT conjugate prepared in the same manner as the Europium complex described hereinbefore.

Examples 1–2 Preparation and Evaluation of
Radionuclide {$^{111}$In and $^{90}$Y) Chelate Complexes
of a TMT Conjugate and, as a Comparative
Control, of a DTPA Conjugate In Vivo Functional Test of Chelate-Antibody Conjugates-Biodistribution Experiments 1. Test Materials. The immunoconjugates tested were a B72.3-TMT conjugate prepared as described above or a B72.3-DTPA conjugate in which the DTPA was attached (through a linker arm) to oxidized carbohydrate on the antibody using procedures similar to those described for TMT attachment.

2. Labeling Conjugates with Radioisotopes. The antibody-chelate conjugates to be labeled with either $^{111}$In or $^{90}$Y were in phosphate buffered saline, pH 6.0. The radionuclides (about 1 mCi) were added to the conjugate solution (1 mL containing about 1 mg of antibody-chelate conjugate), mixed, and incubated about 30 min at room temperature. Any non-chelated metal was removed from each conjugate preparation by HPLC gel filtration (TSK$_{3000}$SW column). The column effluent was monitored for both protein (OD280 nm) and radioactivity (radioactivity monitor). The specific activity of the purified labeled conjugates was calculated from this data. The conjugates were used for biodistribution studies immediately.

3. General Procedure. Five mice were used in each test group for the $^{90}$Y biodistribution study and 3 mice in each group for the In study. Target doses for each mouse were 10 µg of radioactive conjugate per dose, 20–100 mg antibody per µL, greater than 50 µCi per dose. Both non-tumor bearing and tumor bearing mice were injected on Day 0.

4. Tumor Growth Initiation. Each nude mouse (nu/nu: Swiss Background, Taconic Farms, Germantown, N.Y.) was injected subcutaneously in the left rear flank with one million LS174T cells in exponential growth phase, in about 0.2 mL of sterile medium or saline from cell culture. The mice were examined for tumor growth until tumors became measurable. Thereafter, tumors were measured to the nearest 0.1 mm, across two perpendicular diameters (length×width) using digital calipers until the product of the length times the width was between 50 and 100 square millimeters for all the mice.

5. Injection Protocol. On a desirable day following tumor cell inoculation (day 0), each mouse was injected with the labeled conjugate. The radiolabeled antibody for each dose was drawn up into a separate 1 cc insulin syringe with a 28G, ½ inch needle for administration. Three 10 μL aliquots of each test material were saved for gamma counting to determine the injected dose.

Each syringe containing test material was numbered in order of administration. Each syringe was weighed and counted in a dose calibrator set to quantitate the radionuclide. This information was recorded. The mice were anesthetized by injecting i.p. 0.15 mL of a sterile solution containing ketamine HCl at 11 mg/mL and xylazine at 3 mg/mL. The test material was injected via the retroorbital venous sinus. Each mouse was counted in the dose calibrator immediately after injection, and the syringes were reweighed, recounted and the data recorded.

6. Methods of Evaluation. Each animal was weighed to the nearest 0.1 g on Day 0 and just prior to dissection. Immediately prior to imaging and/or dissection, each animal was counted in the dose calibrator following standard operating procedures. Each carcass was counted after dissection. Immediately prior to dissection, each animal had its tumor measured to the nearest 0.1 mm across two perpendicular diameters (length×width) using digital calipers. A blood sample was collected from each animal into a tared culture tube and then the tube was reweighed. Each animal was sacrificed by cervical dislocation. Organs (lungs, spleen, liver, colon, right kidney, left kidney, tumor, bone marrow, muscle) were dissected and trimmed to remove extraneous tissue and then weighed to the nearest milligram. Radioactivity of the dissected organs was determined by gamma counting.

Figure 3:
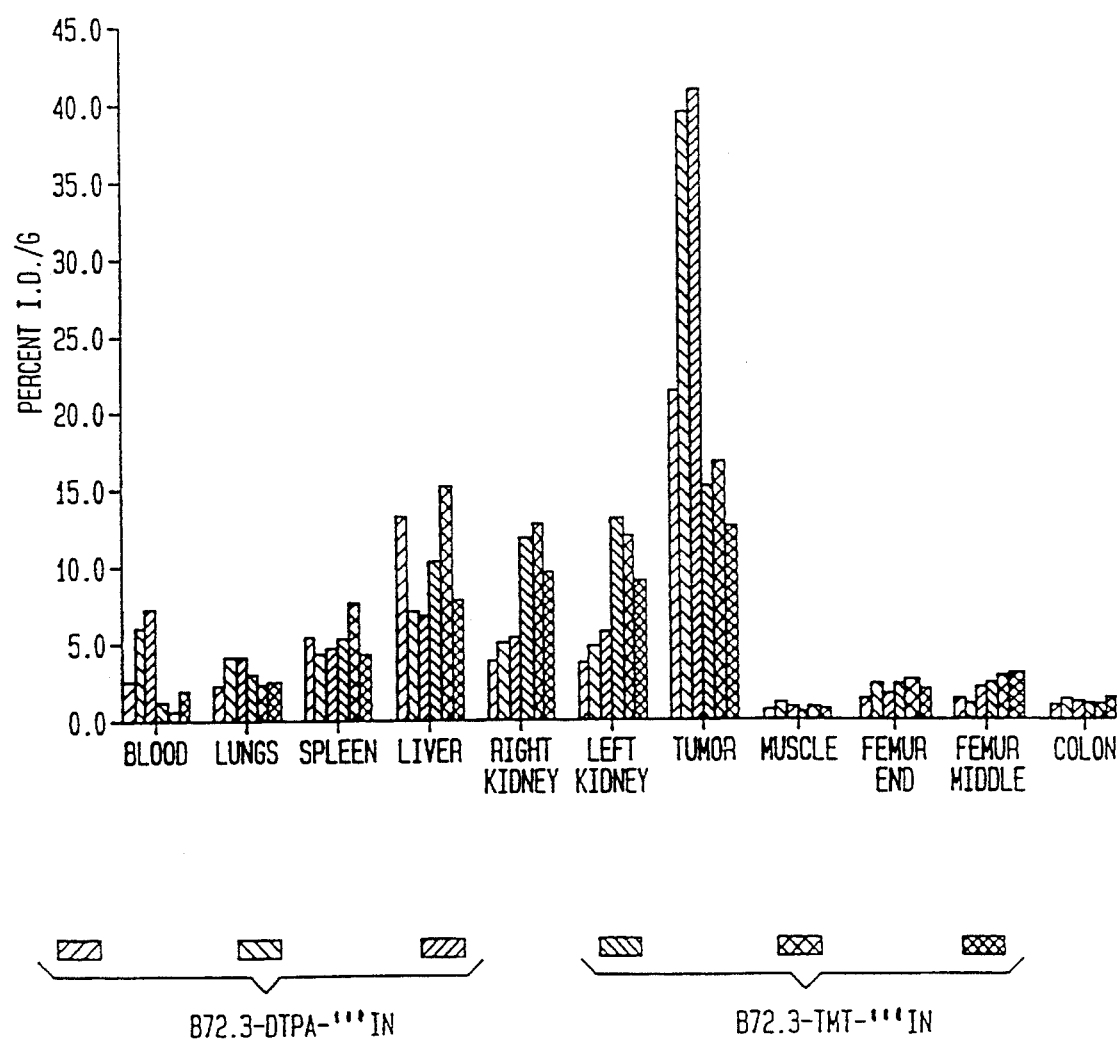
FIG. 3 depicts the results of a biodistribution study of B72.3-TMT-¹¹¹In, a radioactive immunoreagent of the invention, and B72.3-DTPA-¹¹¹In.

7. Results. The biodistributions shown in FIG. 3 are for six mice four days after injection of the radioactive immunoreagents. The data from the $^{111}$In biodistribution test indicate that the radiolabeled TMT conjugate of B72.3 did target the radioactivity to the tumor. Although liver and kidney levels were slightly greater than the B72.3-DTPA-$^{111}$In conjugate, the B72.3 -TMT-$^{111}$In conjugate could be used for $^{111}$In tumor targeting.

Figure 4:
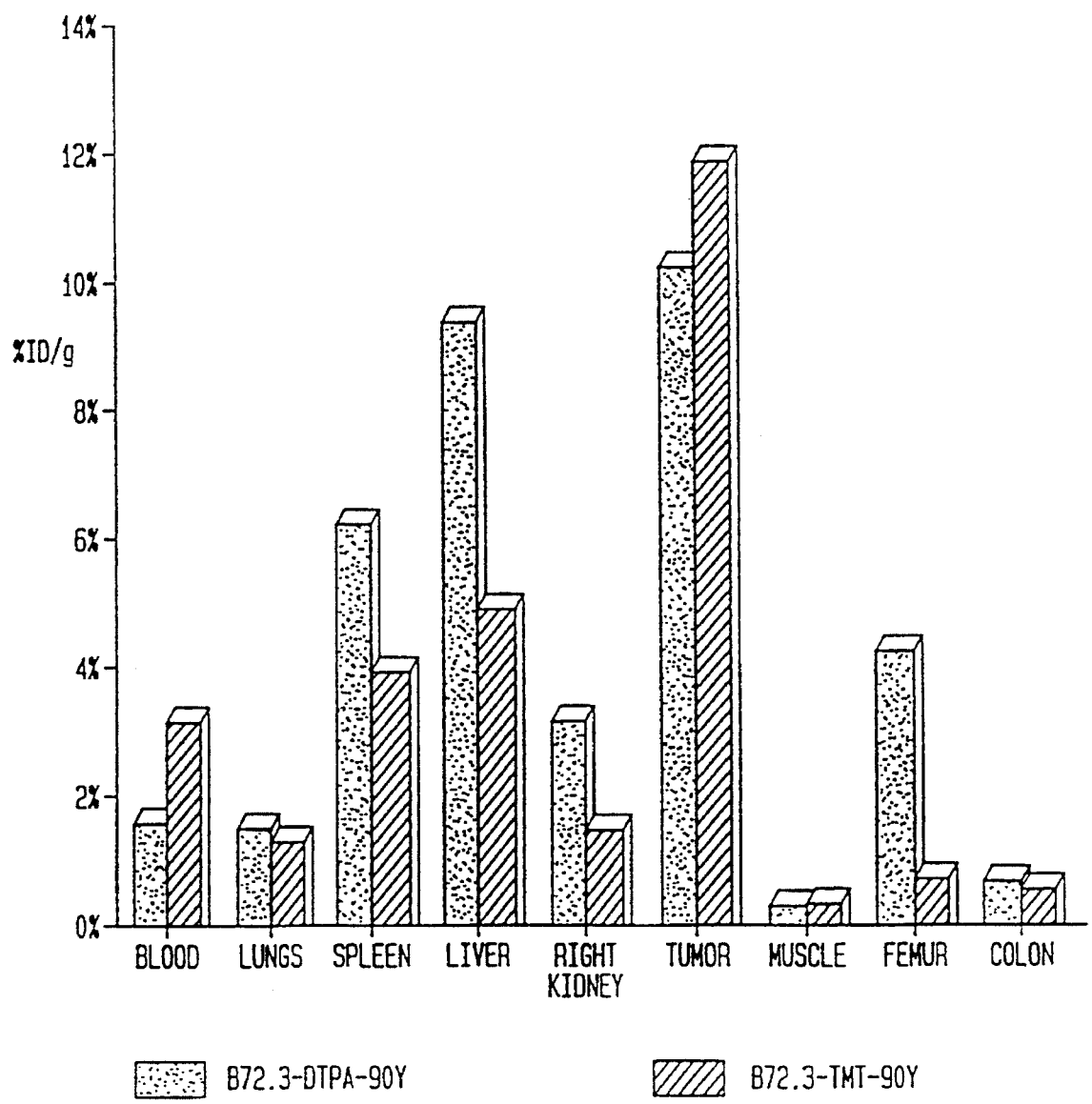
FIG. 4 depicts the results of a biodistribution study of B72.3-TMT-⁹⁰Y, a radioactive immunoreagent of the invention, and B72.3-DTPA-⁹⁰Y.

The biodistrubtions shown in FIG. 4 are eight days after injection of the radioactive immunoreagent. The average value for each group of five mice is graphed for the tissue type examined. The data from the $^{90}$Y biodistribution show that the B72.3-TMT-$^{90}$Y conjugate targeted $^{90}$Y to the tumor as well as the B72.3-DTPA-$^{90}$Y conjugate. However, considerably less $^{90}$Y was found in the femur when the B72.3-TMT-$^{90}$Y conjugate was used compared to the B72.3-DTPA-$^{90}$Y conjugate. Since the femur (bone marrow) is the dose-limiting organ for $^{90}$Y therapy, this result indicates that TMT is a better chelate for antibody targeted radionuclide therapy using this isotope. Of the other tissues examined, only the blood was found to have a higher $^{90}$Y level when TMT was the chelate used to prepare the immunoconjugate. This is believed to be due to superior in vivo stability of the B72.3-TMT-$^{90}$Y complex compared to the B72.3-DTPA-$^{90}$Y complex.

Survival Study

Figure 5:
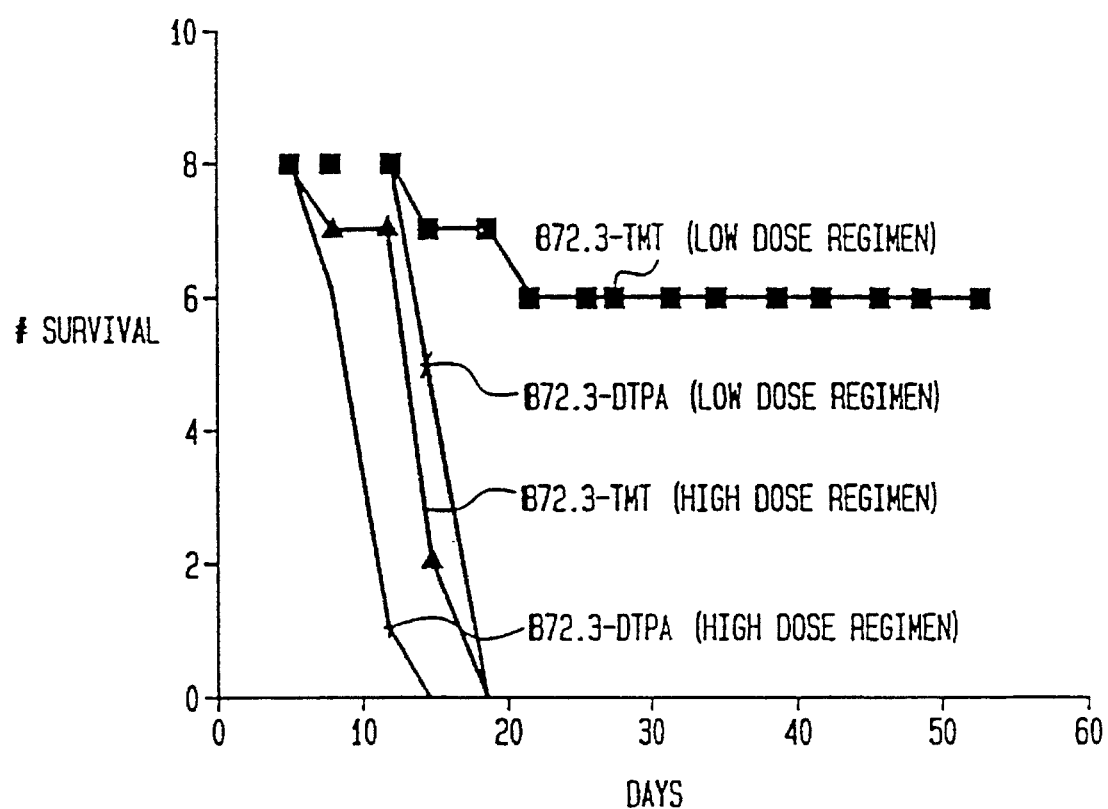
FIG. 5 is the survival curve, i.e., the number of mice surviving each day past the first day of innoculation for a low dose regimen and a high dose regimen.

If the B72.3-TMT-$^{90}$Y complex decreases the amount of $^{90}$Y that gets to the bone marrow compared to B72.3-DTPA-$^{90}$Y and the bone marrow is the dose-limiting tissue, then mice innoculated with the conjugates should find the B72.3-TMT-$^{90}$Y conjugate less toxic than those innoculated with B72.3-DTPA-$^{90}$Y. The general procedures to test this hypothesis (survival study) were the same as those described for the biodistribution study with the following exceptions. There were 8 tumor bearing nude mice in each test group. The injection schedule was as follows: 200 μCi, 120 μCi, and 120 μCi were given on days 0, 4 and 8, respectively, for both the B72.3-TMT-$^{90}$Y or B72.3-DTPA- $^{90}$Y conjugate (low dose regimen). Two other sets of mice received 400 μCi, 320 μCi and 320 μCi of the two immunoconjugates on days 0, 4 and 8, respectively (high dose regimen). The survival of the mice was observed (no biodistributions of the test material were performed). Results (FIG. 5) indicate that the survival of the mice was prolonged if $^{90}$Y is administered using the B72.3-TMT conjugate.

TMT-Immunoconjugate with Anti-tumor Specificity

TMT or a suitable derivative thereof can be conjugated to an antibody molecule to yield an antibody-TMT conjugate molecule that displays the ability to bind to a target antigen recognized by the antibody variable region. Such a conjugate molecule can be used to deliver a radioisotope-that is chelated by the TMT moiety in order to localize and/or treat the lesion that is targeted by such an immunoconjugate. In one preferred embodiment, the antibody is selected such that it has a broad reactivity with an antigen molecule expressed on tumor cells, thereby providing an antibody-TMT conjugate that can deliver radioisotope to the tumors for therapeutic or diagnostic purposes. ING-1 is a chimetic antibody (described in International Patent Publication Number WO 90/02569, dated 22 Mar. 1990) consisting of a murine variable region and a human immunoglobulin constant region. The antibody molecule is produced by culturing a mouse myeloma cell line expressing the chimetic antibody essentially as described in the above-referenced publication. The chimetic ING-1 antibody is used at a concentration of 5.2 mg/ml in 50 mM sodium acetate buffer at pH 5.6 and supplemented with 150 mM NaCl. To 1.15 ml of antibody solution is added a solution of 50 mM sodium borate at pH 9.0 supplemented with 100 mM sodium chloride to a final total volume of 2.5 ml. The solution is applied to a PD-10 chromatography column equilibrated with the sodium borate buffer added to the antibody solution. The antibody is eluted off the column with 3.5 ml of the same sodium borate buffer. The eluate is concentrated using a Centricon-30 to a concentration of approximately 4.0 mg ING-1 chimeric antibody per milliliter solution. The solution of the NCS derivative of TMT (Preparation 6), i.e., TMT wherein the NH$_2$ is replaced with NCS, (designated herein as TMT-NCS) is prepared in the sodium borate buffer at a concentration of 10mg/ml and added to the antibody solution to a final concentration of 138 μM of TMT-NCS. The solution is gently mixed and incubated in the dark at ambient temperature (approx. 22° C.) overnight (approx. 12 hr). The ING-1:TMT conjugate is separated from free TMT-NCS and other low molecular weight products using a Superose 12 HPLC column equilibrated and eluted in 50 mM sodium acetate buffer at pH 5.6 supplemented with 150 mM sodium chloride. The TMT immunoconjugate is then tested for its ability to bind to the tumor cell antigen and also to bind Yttrium-90 isotope to demonstrate that the conjugate can be radiolabeled in the TMT moiety and can target the tumor cell.

The invention has been described in detail with particular reference to certain preferred embodiments thereof, but it

What is claimed is:

1. A compound having the formula:

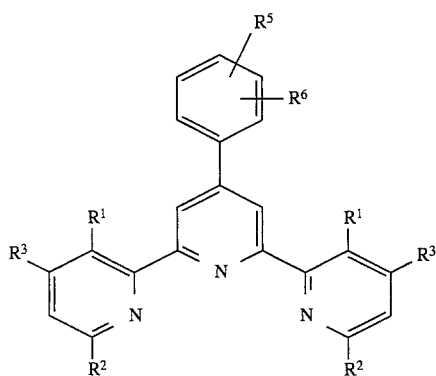

wherein $R^1$ represents hydrogen, alkyl, alkoxy, alkylthio, alkylamino, alkylformamido, aryl, aryloxy, heterocyclyl or a protein reactive group;

the two $R^2$ groups, taken together, represent a bridging group serving complete a macrocyclic ring, the bridging group containing at least one heteroatom and at least one alkylene group which form part of the resulting macrocyclic ring;

$R^3$ represents hydrogen, alkyl, alkoxy, alkylthio, alkylamino, alkylformamido, aryl, aryloxy, heterocyclyl, or a protein reactive group;

$R^5$ represents alkyl or alkoxy; and $R^6$ represents a protein reactive group.

2. The compound of claim 1 wherein $R^5$ is methoxy.

3. The compound of claim 1 wherein $R^6$ is selected from the group consisting of amino, alkylamino, arylamino, carbazido, semicarbazido, thiocarbazido, thiosemicarbazido, isocyanato and isothiocyanato.

4. The compound of claim 1 wherein $R^6$ is selected from the group consisting of amino, isothiocyanato and thiocarbazido.

5. The compound of claim 1 wherein $R^5$ is 3-methoxy and $R^6$ is 4-amino.

6. The compound of claim 1 wherein each $R^3$ is H.

* * * * *